(12) United States Patent
Ishiwata et al.

(10) Patent No.: US 6,297,283 B1
(45) Date of Patent: Oct. 2, 2001

(54) DIAMIDE COMPOUNDS AND COMPOSITIONS CONTAINING THE SAME

(75) Inventors: Hiroyuki Ishiwata, Ichikawa; Mototsugu Kabeya, Higashimurayama; Masami Shiratsuchi, Musashimurayama; Yukio Hattori, Ushiku; Hiroshi Nakao; Takao Nagoya, both of Tsuchiura; Seiichi Sato, Tokyo; Soichi Oda, Higashimurayama; Makoto Suda; Manabu Shibasaki, both of Tsukuba, all of (JP)

(73) Assignee: Kowa Co., Ltd., Nagoya (JP)

( * ) Notice: Subject to any disclaimer, the term of this patent is extended or adjusted under 35 U.S.C. 154(b) by 0 days.

(21) Appl. No.: 09/269,764

(22) PCT Filed: Oct. 8, 1997

(86) PCT No.: PCT/JP97/03603

§ 371 Date: Apr. 9, 1999

§ 102(e) Date: Apr. 9, 1999

(87) PCT Pub. No.: WO98/16497

PCT Pub. Date: Apr. 23, 1998

(30) Foreign Application Priority Data

Oct. 11, 1996 (JP) ................................................. 8-269547

(51) Int. Cl.$^7$ ...................... A61K 31/165; A61K 31/245; C07C 235/34; C07C 235/36; C07C 235/38
(52) U.S. Cl. ........................ 514/616; 514/308; 514/314; 514/332; 514/414; 546/146; 546/175; 546/265; 548/455; 564/155; 564/158
(58) Field of Search ................................. 564/155, 158; 514/616, 308, 314, 332, 414; 546/146, 175, 265; 548/455

(56) References Cited

FOREIGN PATENT DOCUMENTS

| 1-106818 | 4/1989 | (JP) . |
| 7-017506 | 3/1995 | (JP) . |
| 8-092216 | 4/1996 | (JP) . |

OTHER PUBLICATIONS

N. Matsuura, et al., Jpn. Pharmacol. Ther., vol. 22, No. 3, pp. 265–279, "An Immunopharmacological Study of (±)–[2–[4–(3–Ethoxy–2–Hydroxypropoxy)Phenylcarbamoyl] Ethyl]Dimethulsulfonium $_p$–Toluenesulfonate(Suplatast Tosilate, IPD–1151T)," 1994.

Jentgens et al, Chemical Abstracts, vol. 127:176167, 1997.*
Yanagihara et al., Chemical Abstracts, vol. 126:164314, 1997.*
Bonneau et al., Chemical Abstracts, vol. 121:175330, 1994.*
Nakase et al., Chemical Abstracts, vol. 113:90936, 1990.*
Martin–Tanguy et al., Chemical Abstracts, vol. 113:75021, 1990.*
Kurihara et al., Chemical Abstracts, vol. 110:136769, 1989.*
Martin–Tanguy et al., Chemical Abstracts, vol. 90:183150, 1979.*
Kolodynska et al., Chemical Abstracts, vol. 80:36811, 1974.*
Altman et al., Chemical Abstracts, vol. 77:61480, 1972.*
Kolodynska et al., Chemical Abstracts, vol. 68:39585, 1968.*
Basyouni et al., Chemical Abstracts, vol. 95:24223, 1981.*
Werbel et al., Chemical Abstracts, vol. 69:75378, 1968.*
Wakabayashi et al., Chemical Abstracts, vol. 111:23234, 1989.*

* cited by examiner

*Primary Examiner*—Richard L. Raymond
(74) *Attorney, Agent, or Firm*—Oblon, Spivak, McClelland, Maier & Neustadt, P.C.

(57) ABSTRACT

The present invention relates to compounds represented by the following general formula (1):

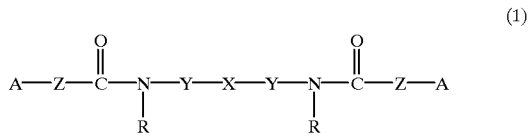

wherein A is a phenyl, naphthyl, dihydronaphthyl, indenyl, pyridyl, indolyl, isoindolyl, quinolyl or isoquinolyl group which may be substituted; X is a lower alkylene group which may be substituted, or the like; Y is a single bond or an alkylene group; Z is a group of —CH=CH—, —C≡C—, —(CH=CH)$_2$—, —C≡C—CH=CH— or —CH=CH—C≡C—, or the like; and R is a hydrogen atom, a lower alkyl group or the like, and medicines comprising such a compound. These compounds have an excellent inhibitory effect on the production of an IgE antibody and are hence useful as antiallergic agents and the like.

18 Claims, No Drawings

DIAMIDE COMPOUNDS AND COMPOSITIONS CONTAINING THE SAME

This application is a 371 of PCT/JP97/03603, filed Oct. 8, 1997.

BACKGROUND OF THE INVENTION

1. Field of the Invention

The present invention relates to novel diamide compounds and medicines useful in preventing and treating allergic immunological diseases, comprising such a compound as an active ingredient.

2. Description of the Background

IgE, which is a kind of immunoglobulin (Ig), is an allergen-specific molecule produced by an IgE producing cell differentiated from a B cell. This process is triggered by the contact of an immunocyte with an allergen in vivo.

IgE is produced in a target organ for an allergy and binds to a receptor on the surface of a mast cell, which is a central effector cell in an allergic reaction, or a basophil (sensitized state). After the sensitization, allergic chemical mediators such as histamine, leukotrienes, prostaglandins and PAF, and injuring enzymes such as tryptase are released from the mast cell stimulated by the reaction of the specific IgE and the allergen which invades in the living body, so that immediate responses, such as vascular permeability acceleration, smooth muscle constriction, and vasodilation are elicited. Further, cytokines such as IL-4, which directly activate other immune system cells, are also secreted from the stimulated mast cell. As a result, eosinophils, basophils and the like infiltrate into a tissue, and the allergic chemical mediators and tissue injuring proteins such as MBP, which are secreted by these inflammatory cells, induce a late response, so that the allergic symptom is lingered and taken seriously ill.

From this, IgE is considered a substance fundamentally participating in the attack of an allergic immunological disease.

Therefore, several compounds having an inhibitory effect on the production of an IgE antibody have heretofore been found and reported with a view toward developing antiallergic agents [Pharmacology and Therapy, 1994, 22(3), 1369; Japanese Patent Application Laid-Open No. 106818/1989; Japanese Patent Publication No. 17506/1995; and Japanese Patent Application Laid-Open No. 92216/1996]. However, the object has been not always sufficiently achieved under the circumstances.

SUMMARY OF THE INVENTION

Accordingly, it is an object of the present invention to find a compound having a strong inhibitory effect on the production of an IgE antibody so as to provide a medicine effective for allergic immunological diseases, comprising this compound as an active ingredient.

DETAILED DESCRIPTION OF THE PREFERRED EMBODIMENTS

With the foregoing circumstances in view, the present inventors have carried out an extensive investigation. As a result, it has been found that novel diamide compounds represented by the general formula (1), which will be described subsequently, salts thereof, or solvates thereof have an excellent inhibitory effect on the production of an IgE antibody and are useful as prophylactic and therapeutic agents for various allergic immunological diseases, thus leading to completion of the present invention.

According to the present invention, there is thus provided a compound represented by the following general formula (1):

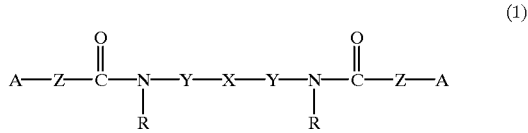

wherein A is a phenyl, naphthyl, dihydronaphthyl, indenyl, pyridyl, indolyl, isoindolyl, quinolyl or isoquinolyl group which may be substituted;

X is a lower alkylene group which may be substituted; a divalent residue of an alicyclic compound which may be substituted, an aromatic compound which may be substituted, or a heterocyclic compound which may be substituted; an imino group which may be substituted; or a sulfur atom or an oxygen atom;

Y is a single bond or a lower alkylene group;

Z is a group of —CH=CH—, —C≡C—, —(CH=CH)$_2$—, —C≡C—CH=CH— or —CH=CH—C≡C—, or a divalent residue of benzene, pyridine, pyrimidine or pyrazine which may be substituted; and R is a hydrogen atom, or a lower alkyl, cycloalkyl, aryl or aralkyl group, with the proviso that A is not a phenyl group, a 4-chlorophenyl group nor a 4-methoxyphenyl group when X is an ethylene group, Y is a single bond, Z is —C≡C—, and R is a hydrogen atom; A is not a 3,4-dichlorophenyl group when X is a trimethylene group, Y is a single bond, Z is —(CH=CH)$_2$—, and R is a hydrogen atom; and A is not a 3,4-dihydroxyphenyl group, a 3-hydroxy-4-methoxyphenyl group, a 3-methoxy-4-hydroxyphenyl group nor a 3,4-dimethoxyphenyl group when X is a tetramethylene group, Y is a single bond, Z is —CH=CH— or —(CH=CH)$_2$—, and R is a hydrogen atom, a salt thereof, or a solvate thereof.

According to the present invention, there is also provided a medicine comprising the above compound as an active ingredient.

According to the present invention, there is further provided a medicinal composition comprising the above compound and a pharmaceutically acceptable carrier.

According to the present invention, there is still further provided use of the above compound for a medicine.

According to the present invention, there is yet still further provided a method of treating an allergic immunological disease, which comprises administering an effective amount of the above compound.

BEST MODE FOR CARRYING OUT THE INVENTION

The diamide compounds according to the present invention are represented by the general formula (1). As compounds similar to these compounds, 5-phenyl-2,4-pentadiene derivatives are described in J. Med. Chem., 1968, 11, 1073. However, these compounds are described only as antimalarial drugs, not as antiallergic agents. Japanese Patent Application Laid-Open No. 214766/1985 also describes compounds similar to the compounds (1) according to the present invention. However, the publication describes these compounds as 5-lipoxygenase inhibitors, but does not describe anything about the fact that they have an inhibitory effect on the production of an IgE antibody.

In the present invention, "alkyl" in alkyl groups, alkylamino groups, dialkylamino groups and the like means linear or branched alkyl generally having 1–12 carbon atoms, and lower alkyl groups are preferred. The lower alkyl groups include linear or branched alkyl groups having 1–8 carbon atoms. Specific examples thereof include methyl, ethyl, n-propyl, i-propyl, n-butyl, i-butyl, sec-butyl, tert-butyl, pentyl, hexyl, heptyl and octyl groups. Of these, those having 1–6 carbon atoms, for example, methyl, ethyl, propyl, i-propyl, n-butyl, i-butyl, tert-butyl, n-pentyl and n-hexyl groups, are particularly preferred.

"Alkoxy" in alkoxy groups, alkoxycarbonyl groups and the like means linear or branched alkoxy generally having 1–12 carbon atoms, and lower alkoxy groups are preferred. The lower alkoxy groups include linear or branched alkoxy groups having 1–8 carbon atoms. Specific examples thereof include methoxy, ethoxy, n-propoxy, i-propoxy, n-butoxy, i-butoxy, sec-butoxy, tert-butoxy, pentyloxy, hexyloxy, heptyloxy and octyloxy groups. Of these alkoxy groups, those having 1–6 carbon atoms are preferred.

Lower alkylene groups include linear or branched alkylene groups having 1–8 carbon atoms. Specific examples thereof include methylene, ethylene, propylene, trimethylene, tetramethylene, pentamethylene, hexamethylene, heptamethylene and octamethylene groups.

Alicyclic compounds include saturated alicyclic hydrocarbons having 3–8 carbon atoms, for example, cycloalkanes such as cyclopentane, cyclohexane, cycloheptane and cyclooctane.

Aromatic compounds include aromatic compounds having 6–14 carbon atoms, such as benzene and naphthalene.

Heterocyclic compounds include 5- to 7-membered heterocyclic compounds containing 1–3 nitrogen atoms, such as pyrrolidine, pyridine, piperidine, piperazine and homopiperazine.

Cycloalkyl groups include cycloalkyl groups having 3–8 carbon atoms, such as cyclopropyl, cyclobutyl, cyclopentyl, cyclohexyl, cycloheptyl and cyclooctyl groups.

Aryl groups include aromatic groups having 6–14 carbon atoms, such as phenyl and naphthyl groups. Aralkyl groups include $C_{6-14}$-aryl- $C_{1-8}$-alkyl groups such as benzyl, phenylethyl and naphthylmethyl groups.

Alkylthio groups include alkylthio groups having 1–8 carbon atoms.

Halogen atoms include fluorine, chlorine, bromine and iodine atoms.

In the formula (1), A is a phenyl, naphthyl, dihydronaphthyl, indenyl, pyridyl, indolyl, isoindolyl, quinolyl or isoquinolyl group. These groups may have 1–3 substituents. Here, examples of the substituents on these groups include a hydroxyl group, halogen atoms, lower alkyl groups which may be substituted by 1–3 halogen atoms, lower alkoxy groups, an amino group which may be substituted by one or two lower alkyl groups, and alkylthio groups. As A, a phenyl group substituted by 1–3 substituents selected from among lower alkyl groups and lower alkoxy groups is particularly preferred.

The lower alkylene group represented by X is preferably a linear or branched alkylene group having 1–8 carbon atoms. A linear alkylene group having 5–8 carbon atoms is more preferred, with a hexamethylene group being particularly preferred. It is also preferred that X be an ethylene group. These groups may have a substituent such as a halogen atom, or a hydroxyl, lower alkoxy, carboxyl or lower alkoxycarbonyl group. Of these, a lower alkylene group which may be substituted by a carboxyl or lower alkoxycarbonyl group is particularly preferred.

The divalent residue of the alicyclic compound, which is represented by X, is preferably a divalent residue of a cycloalkane having 5–8 carbon atoms. Examples of the divalent residue of the aromatic compound, which is represented by X, include phenylene and naphthylene groups, with a phenylene group being particularly preferred. Here, the phenylene group may be any of 1,2-phenylene, 1,3-phenylene and 1,4-phenylene groups, with a 1,2-phenylene or 1,4-phenylene group being particularly preferred. Preferable examples of the divalent residue of the heterocyclic compound, which is represented by X, include divalent residues of pyridine, pyrrolidine, piperidine, piperazine, homopiperazine and the like. The divalent residue of the alicyclic compound, aromatic compound or heterocyclic compound, or the imino group, which is represented by X, may be substituted by a halogen atom, a hydroxyl group, a lower alkyl group which may be substituted by a primary, secondary or tertiary amino group, a lower alkoxy group, a carboxyl group, a lower alkoxy-carbonyl group, an amino group, an alkylamino group, a dialkylamino group, a nitro group, a cyano group, an aralkyl group, or the like. Here, examples of the primary, secondary or tertiary amino group include amino, lower alkylamino and di-lower alkylamino groups.

X is preferably the divalent residue of the alicyclic compound which may be substituted, the divalent residue of the aromatic compound which may be substituted, or the divalent residue of the heterocyclic compound which may be substituted.

The lower alkylene group represented by Y is preferably a linear or branched alkylene group having 1–8 carbon atoms.

Examples of groups which may be substituted on the divalent residue of benzene, pyridine, pyrimidine or pyrazine represented by Z include halogen atoms, and lower alkyl, lower alkoxy, amino and nitro groups.

R is preferably a hydrogen atom, or a lower alkyl, cycloalkyl, phenyl or aralkyl group, with a hydrogen atom, a lower alkyl group, a cycloalkyl group having 5–8 carbon atoms, a phenyl group, a benzyl group or a phenylethyl group being particularly preferred.

In the formula (1), A is not a phenyl group, a 4-chlorophenyl group nor a 4-methoxyphenyl group when X is an ethylene group, Y is a single bond, Z is —C≡C—, and R is a hydrogen atom. Also, A is not a 3,4-dichlorophenyl group when X is a trimethylene group, Y is a single bond, Z is —(CH=CH)$_2$—, and R is a hydrogen atoms. Further, A is not a 3,4-dihydroxyphenyl group, a 3-hydroxy-4-methoxyphenyl group, a 3-methoxy-4-hydroxyphenyl group nor a 3,4-di-methoxyphenyl group when X is a tetramethylene group, Y is a single bond, Z is —CH=CH— or —(CH=CH)$_2$—, and R is a hydrogen atom.

Among the above-described compounds, compounds obtained in Examples 3, 5, 13, 15, 22, 26, 29, 48, 49, 51, 55 and 57, which will be described subsequently, are particularly preferred in the present invention.

No particular limitation is imposed on the salts of the diamide compounds (1) according to the present invention so far as they are pharmaceutically acceptable salts. In the case where the diamide compounds (1) are basic compounds, however, examples of the salts include mineral acid salts such as hydrochlorides and sulfates; organic acid salts such as methanesulfonates, acetates, oxalates and citrates. In the case where the diamide compounds (1) are acidic compounds on the other hand, examples of the salts include alkali metal salts such as sodium salts and potassium salts; alkaline earth metal salts such as calcium salts and magnesium salts; and organic basic salts such as pyridine salts, picoline salts and triethylamine salts.

The diamide compounds (1) may be present in the form of solvates such as hydrates.

The diamide compounds (1) can be prepared according to, for example, the following reaction formula:

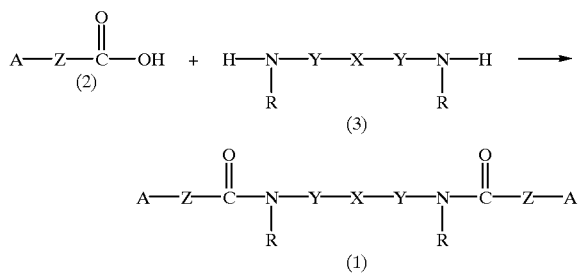

wherein A, X, Y, Z and R have the same meanings as defined above.

More specifically, the compounds (1) according to the present invention are obtained by the N-acylating reaction of a carboxylic acid (2) with a diamine (3).

The N-acylating reaction may be conducted by using any N-acylating reaction known per se in the art. It is particularly preferable to apply, for example, (a) a method in which the carboxylic acid (2) and the diamine (3) are reacted in the presence of a condensation reagent, preferably, a base and a condensation reagent in a solvent, or (b) a method in which a reactive derivative of the carboxylic acid (2) and the diamine (3) are reacted in a solvent.

Examples of the solvents used in these reactions may include dimethylformamide, tetrahydrofuran, dioxane, acetonitrile, methylene chloride and dichloroethane. As the base, may be used an organic base such as pyridine, triethylamine or diisopropylethylamine, or an inorganic base such as sodium carbonate or sodium hydrogencarbonate. Examples of usable condensation agents include 1,3-dicyclohexylcarbodiimide, 1-cyclohexyl-3-morpholinoethylcarboduimide, 1-(3-dimethylaminopropyl)-3-ethylcarbodiimide, 1,1'-carbonyldiimidazole, diethyl phosphorocyanidate, diphenylphosphoryl azide, bis(2-oxo-3-oxazolidinyl)-phosphinic chloride and 2-chloro-1-methylpyridinium iodide. Examples of usable derivatives of the carboxylic acid include acid halides such as acid chlorides, acid azides, symmetric acid anhydrides, mixed anhydrides with pivalic acid or the like, and active esters such as cyanomethyl esters and p-nitrophenyl esters.

In each of the method (a) and the method (b), the N-acylating reaction is completed by reacting the carboxylic acid (2) with the diamine (3) at a reaction temperature of 0° C. to 100° C. for 30 minutes to 30 hours. The isolation and purification of the compound (1) from the reaction mixture may be conducted by using any methods known per se in the art, for example, filtration, extraction, washing, drying, concentration, recrystallization and various kinds of chromatography.

The compound (1) thus obtained may be converted into an acid-addition salt or a basic salt in a method known per se in the art.

The compound may also be converted into a solvate with a solvent for recrystallization, or the like, in particular, a hydrate.

Since the diamide compounds (1) according to the present invention have an excellent inhibitory effect on the production of an IgE antibody as demonstrated in Examples, which will be described subsequently, they are useful as medicines for prevention and treatment of various allergic immunological diseases, in which IgE participates, for example, asthma, atopic dermatitis, allergic rhinitis, inflammatory large bowel diseases, contact dermatitis and allergic ophthalmopathy.

The diamide compounds (1) or the salts thereof according to the present invention can be formulated into various oral and parenteral preparations in the form of a solid, semisolid or liquid by adding a pharmaceutically acceptable, inorganic or organic carrier in accordance with a method known per se in the art.

Examples of the oral preparations include tablets, pills, granules, soft and hard capsules, powders, grains, triturations, emulsions, syrups, pellets and elixirs. Examples of the parenteral preparations include injections, drops, infusions, ointments, lotions, tonics, sprays, suspensions, oils, emulsions, suppositories and eye drops. The active ingredients according to the present invention may be formulated into various preparations in accordance with a method known per se in the art. In these preparations, may be suitably used surfactants, excipients, colorants, smell corrigents, preservatives, stabilizers, buffers, suspension stabilizers, isotonic agents and the like, as needed.

The dose of the diamide compound (1) or the salt thereof varies according to the kind of the compound, the kind of a disease to be treated or prevented, an administration method, the condition, age, sex, weight of a patient to be administered, treatment time, and the like. However, the compound may be administered in a dose of 0.01–1,000 mg/kg of weight/day. The compound may be administered at once or in several portions, for example, 2 to 6 portions a day.

EXAMPLES

The present invention will hereinafter be described in more detail by the following Examples. However, the present invention is not limited to these examples.

Example 1

Preparation of N,N'-bis[5-(3,4,5-trimethoxyphenyl)penta-(2E,4E)-dienoyl]ethylenediamine:

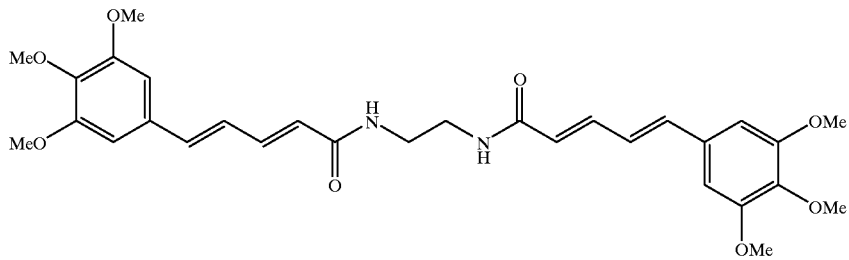

A solution of 196 mg (0.74 mmol) of ethylenediamine in anhydrous dimethylformamide (0.9 ml) was cooled in an ice bath, and to the solution were added 29.4 mg (0.34 mmol) of 5-(3,4,5-trimethoxyphenyl)penta-(2E,4E)-dienoic acid, 0.12 ml (0.86 mmol) of triethylamine and 0.11 ml (0.74 mmol) of diethyl phosphorocyanidate. The ice bath was removed, and the mixture was stirred for 1 hour at room temperature. Added to the reaction mixture was a 5% aqueous solution (4 ml) of sodium hydrogencarbonate to conduct extraction with chloroform. An organic layer was dried over anhydrous sodium sulfate and then concentrated under reduced pressure. The resultant crude oil (274 mg) was purified by column chromatography on alumina and column chromatography on silica gel, thereby obtaining 147 mg (yield: 76%) of the title compound as a colorless crystalline powder.

Melting point: 213–214° C.

$^1$H-NMR (DMSO-$d_6$, 120° C.) δ: 3.29 (br s,4H), 3.72(s, 6H), 3.82(2,12H), 6.11(d,J=15.0 Hz,2H), 6.79(d,J=15.5 Hz,2H), 6.81(s,4H), 6.89(dd,J=15.5,9.9 Hz,2H), 7.17(dd,J=15.0,9.9 Hz,2H), 7.66(br s,2H).

Example 2
Preparation of N,N'-bis[5-(3,4,5-trimethoxyphenyl)penta-(2E,4E)-dienoyl]-N,N'-dimethylethylenediamine:

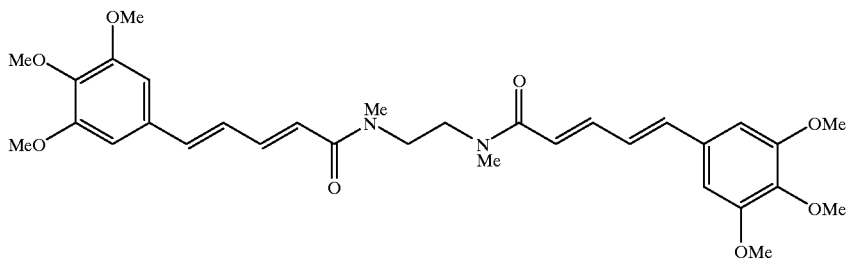

In accordance with the same process as in Example 1, 147 mg (yield: 76%) of the title compound was obtained as a colorless amorphous powder from 198 mg (0.75 mmol) of 5-(3,4,5-trimethoxyphenyl)penta-(2E,4E)-dienoic acid and 29 mg (0.33 mmol) of N,N'-dimethylethylenediamine.

$^1$H-NMR (DMSO-$d_6$, 120° C.) (mixture of amide rotamers) δ: 3.01(s,6H), 3.58(s,4H), 3.71(s,6H), 3.80(s, 12H), 6.50–6.85(m,4H), 6.77(s,4H), 6.92(dd,J=15.3,10.4 Hz,2H), 7.20(dd,J=14.6,10.4 Hz,2H).

Example 3
Preparation of N,N'-bis[5-(3,4,5-trimethoxyphenyl)penta-(2E,4E)-dienoyl]-N,N'-dibenzylethylenediamine:

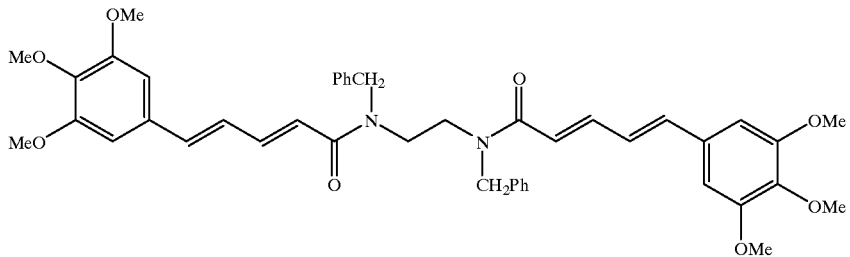

In accordance with the same process as in Example 1, 286 mg (yield: 94%) of the title compound was obtained as a colorless amorphous powder from 241 mg (0.91 mmol) of 5-(3,4,5-trimethoxyphenyl)penta-(2E,4E)-dienoic acid and 100 mg (0.42 mmol) of N,N'-dibenzylethylenediamine.

$^1$H-NMR (DMSO-$d_6$, 120° C.) δ: 3.51(s,4H), 3.71(s,6H), 3.80(s,12H), 4.61(s,4H), 6.59(d,J=14.4 Hz,2H), 6.78(s,4H), 6.82(d,J=15.4 Hz,2H), 6.91(dd,J=15.4,9.5 Hz,2H), 7.18–7.36(m,12H).

Example 4
Preparation of N,N'-bis[5-(3,4,5-trimethoxyphenyl)penta-(2E,4E)-dienoyl]-N,N'-diphenyl-1,3-diaminopropane:

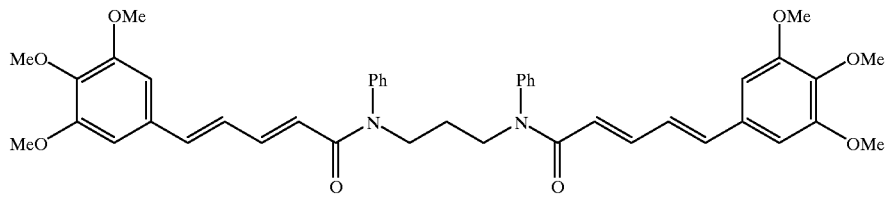

A solution of 174 mg (0.66 mmol) of 5-(3,4,5-trimethoxyphenyl)penta-(2E,4E)-dienoic acid in anhydrous dimethylformamide-methylene chloride (0.1 ml–5 ml) was cooled in an ice bath, and to the solution was added 0.080 ml (0.92 mmol) of oxalyl chloride with stirring. The ice bath was removed, and the mixture was stirred for 30 minutes at room temperature. The reaction mixture was concentrated under reduced pressure to obtain crude crystals of 5-(3,4,5-trimethoxyphenyl)penta-(2E,4E)-dienoyl chloride.

A solution of 5-(3,4,5-trimethoxyphenyl)penta-(2E,4E)-dienoyl chloride in methylene chloride (3 ml) was added dropwise to a solution of 68 mg (0.30 mmol) of N,N'-diphenyl-1,3-diaminopropane in pyridine (3 ml) with stirring in an ice bath. After completion of the addition, the mixture was stirred for an additional 1 hour, and a 5% aqueous solution (5 ml) of sodium hydrogencarbonate was added to the reaction mixture to conduct extraction with chloroform. An organic layer was dried over anhydrous sodium sulfate and then concentrated under reduced pressure. The resultant crude oil (278 mg) was purified by column chromatography on silica gel, thereby obtaining 126 mg (yield: 59%) of the title compound as a colorless amorphous powder.

$^1$H-NMR (DMSO-$d_6$, 120° C.) δ: 1.73 (br quint,J=7.3 Hz,2H), 3.70(s,6H), 3.75(br t,J=7.3 Hz,4H), 3.77(s,12H), 5.87(d,J=14.7 Hz,2H), 6.68–6.83(m,4H), 6.76(s,4H), 7.15–7.28(m,6H), 7.31–7.47(m,6H).

Example 5
Preparation of N,N'-bis[5-(3,4,5-trimethoxyphenyl)penta-(2E,4E)-dienoyl]-N,N'-dimethyl-1,6-diaminohexane:

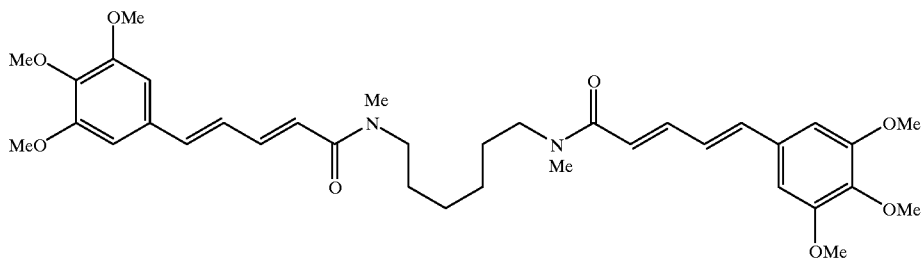

In accordance with the same process as in Example 1, 194 mg (yield: 94%) of the title compound was obtained as a colorless amorphous powder from 170 mg (0.64 mmol) of 5-(3,4,5-trimethoxyphenyl)penta-(2E,4E)-dienoic acid and 47 mg (0.32 mmol) of N,N'-dimethyl-1,6-diaminohexane.

$^1$H-NMR (DMSO-$d_6$, 120° C.) δ: 1.27–1.39(m,4H), 1.55 (br tt,J=7.2,7.2 Hz,4H), 2.96(s,6H), 3.37(br t,J=7.2 Hz,4H), 3.72(s,6H), 3.81(s,12H), 6.57(d,J=14.6 Hz,2H), 6.79(d,J=15.5 Hz,2H), 6.80(s,4H), 6.96(dd,J=15.5,10.8 Hz,2H), 7.19 (dd,J=14.6,10.8 Hz,2H).

Example 6
Preparation of N,N'-bis[5-(3,4,5-trimethoxyphenyl)penta-(2E,4E)-dienoyl]-N,N'-dibenzyl-1,6-diaminohexane:

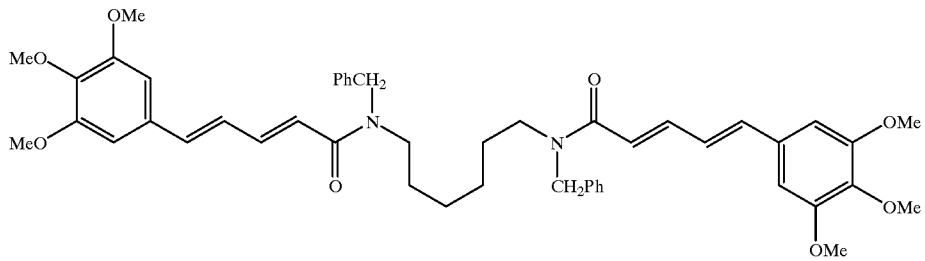

In accordance with the same process as in Example 1, 165 mg (yield: 77%) of the title compound was obtained as a colorless amorphous powder from 147 mg (0.56 mmol) of 5-(3,4,5-trimethoxyphenyl)penta-(2E,4E)-dienoic acid and 100 mg (0.27 mmol) of N,N'-dibenzyl-1,6-diaminohexane dihydrochloride.

$^1$H-NMR (DMSO-$d_6$, 120° C.) δ: 1.18–1.31(m,4H), 1.41–1.56(m,4H), 3.33(br t,J=7.4 Hz,4H), 3.72(s,6H), 3.80 (s,12H), 4.61(s,4H), 6.60(d,J=14.7 Hz,2H), 6.80(s,4H), 6.81 (d,J=15.6 Hz,2H), 6.69(dd,J=15.6,10.5 Hz,2H), 7.18–7.35 (m,12H).

Example 7
Preparation of N,N'-bis[5-(3,4,5-trimethoxyphenyl)penta-(2E,4E)-dienoyl]-N,N'-dicyclohexyl-1,6-diaminohexane:

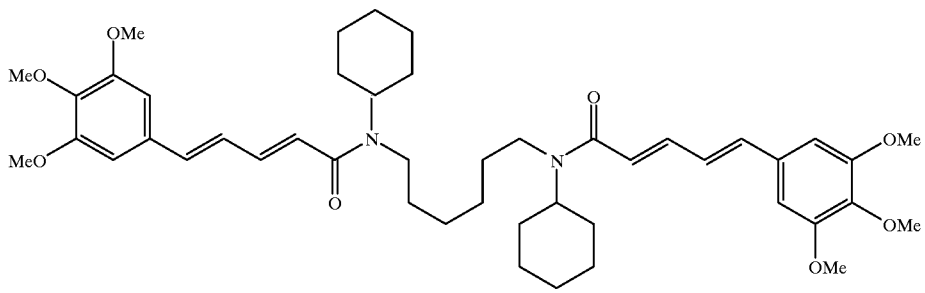

In accordance with the same process as in Example 1, 167 mg (yield: 75%) of the title compound was obtained as a pale brown amorphous powder from 154 mg (0.58 mmol) of 5-(3,4,5-trimethoxyphenyl)penta-(2E,4E)-dienoic acid and 102 mg (0.29 mmol) of N,N'-dicyclohexyl-1,6-diaminohexane dihydrochloride.

$^1$H-NMR (DMSO-$d_6$, 120° C.) δ: 1.03–1.83(m,28H), 3.25 (br t,J=7.7 Hz,4H), 3.72(s,6H), 3.81(s,12H), 3.85–4.01(m, 2H), 6.55(d,J=14.7 Hz,2H), 6.78(d,J=15.4 Hz,2H), 6.80(s, 4H), 6.97(dd,J=15.4,10.7 Hz,2H), 7.20(d,J=14.7,10.7 Hz,2H).

Example 8
Preparation of N,N'-bis[5-(3,4,5-trimethoxyphenyl)penta-(2E,4E)-dienoyl]-N,N'-diphenyl-1,6-diaminohexane:

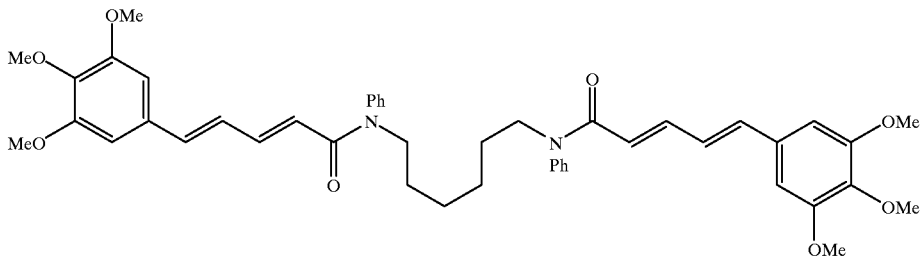

In accordance with the same process as in Example 4, 149 mg (yield: 59%) of the title compound was obtained as a colorless amorphous powder from 174 mg (0.66 mmol) of 5-(3,4,5-trimethoxyphenyl)penta-(2E,4E)-dienoic acid and 89 mg (0.33 mmol) of N,N'-diphenyl-1,6-diaminohexane.

$^1$H-NMR (DMSO-$d_6$, 120° C.) δ: 1.19–1.33(m,4H), 1.38–1.52(m,4H), 3.70(br t,J=7.3 Hz,4H), 3.70(s,6H), 3.77 (s,12H), 5.90(d,J=14.7 Hz,2H), 6.69–6.82(m,4H), 6.76(s, 4H), 7.16–7.48(m,12H).

Example 9
Preparation of Nα,Nε-bis[5-(3,4,5-trimethoxyphenyl)penta-(2E,4E)-dienoyl]-lysine methyl ester:

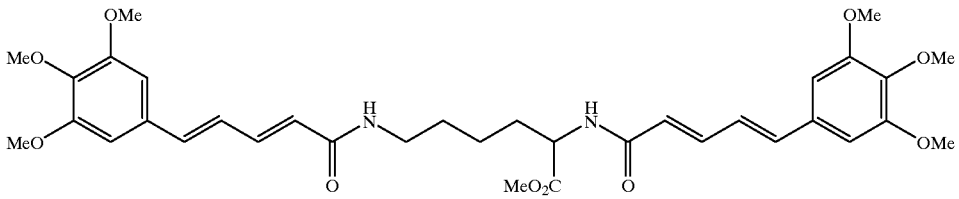

In accordance with the same process as in Example 1, 451 mg (yield: 69%) of the title compound was obtained as a colorless amorphous powder from 529 mg (2.0 mmol) of 5-(3,4,5-trimethoxyphenyl)penta-(2E,4E)-dienoic acid and 233 mg (1.0 mmol) of lysine methyl ester dihydrochloride.

$^1$H-NMR (CDCl$_3$) (mixture of amide rotamers) δ: 1.32–1.53(m,2H), 1.53–1.68(m,2H), 1.68–2.00(m,2H), 3.27–3.45(m,2H), 3.75(s,3H), 3.75–3.90(s,18H), 4.62–4.74 (m,1H), 6.05(br d,J=15.0 Hz,1H), 6.14(br d,J=15.0 Hz,1H), 6.25–6.44(m,1H), 6.61(s,2H), 6.33(s,2H), 6.68–6.87(m,5H), 7.00–7.47(m,2H).

Example 10
Preparation of Nα,Nε-bis[5-(3,4,5-trimethoxyphenyl)penta-(2E,4E)-dienoyl]-lysine:

Added to a solution of 265 mg (0.40 mmol) of Nα,Nε-bis[5-(3,4,5-trimethoxyphenyl)penta-(2E,4E)-dienoyl]-lysine methyl ester synthesized by the process of Example 9 in methanol-tetrahydrofuran (1 ml–1 ml) was 1.0 ml (5.0 mmol) of a 5N aqueous solution of potassium hydroxide, and the mixture was stirred for 3 hours at room temperature. A saturated saline solution (3 ml) and concentrated hydrochloric acid (0.5 ml) were added to the reaction mixture to conduct extraction with chloroform. An organic layer was dried over anhydrous sodium sulfate and then concentrated under reduced pressure. The resultant crude oil (234 mg) was purified by column chromatography on silica gel to obtain 203 mg (yield: 80%) of the title compound as a colorless amorphous powder.

$^1$H-NMR (DMSO-$d_6$) δ: (no OH proton of the carboxyl group was observed): 1.22–1.53(m,4H), 1.53–1.87(m,2H), 3.03–3.20(m,2H), 3.67(s,6H), 3.79(s,12H), 4.10–4.28(m, 1H), 6.13(br d,J=14.8 Hz,1H), 6.32(br d,J=14.8 Hz,1H), 6.78(br d,J=15.2 Hz,1H), 6.79(br d,J=15.2 Hz,1H), 6.82(br s,2H), 6.83(br s, 2H), 6.99(br dd,J=15.2,11.0 Hz,2H), 7.17 (br dd,J=14.8,11.0 Hz,2H), 7.80–7.95(m,1H), 8.05–8.15(m, 1H).

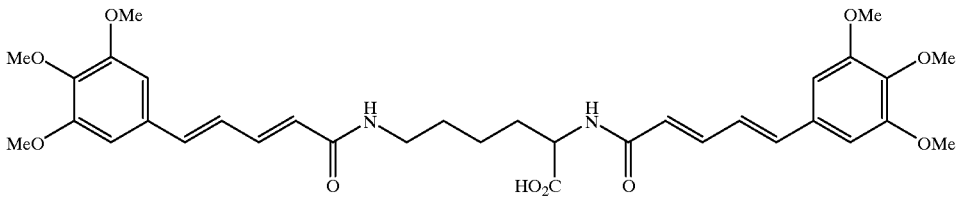

Example 11

Preparation of N,N'-bis[5-(3,4,5-trimethoxyphenyl)penta-(2E,4E)-dienoyl]-1,4-bis(aminomethyl)cyclohexane:

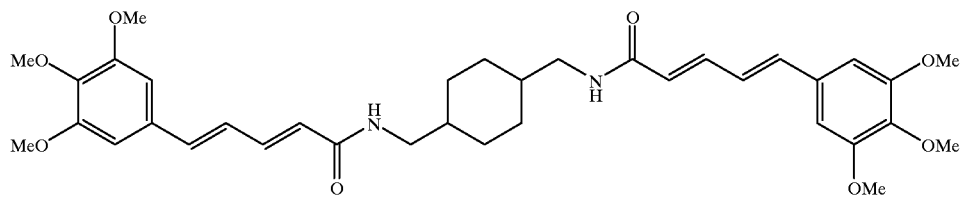

In accordance with the same process as in Example 1, 114 mg (yield: 18%) of the title compound was obtained as a colorless amorphous powder from 555 mg (2.1 mmol) of 5-(3,4,5-trimethoxyphenyl)penta-(2E,4E)-dienoic acid and 142 mg (1.0 mmol) of 1,4-bis(aminomethyl)cyclohexane.

$^1$H-NMR (DMSO-$d_6$, 120° C.) δ: 1.29–1.52(m,8H), 1.52–1.80(m,2H), 3.13(dd,J=6.5,6.5 Hz,4H), 3.72(s,6H), 3.82(s,12H), 6.14(d,J=15.0 Hz,2H), 6.78(d,J=15.4 Hz,2H), 6.80(s,4H), 6.87(dd,J=15.4,9.7 Hz,2H), 7.14(dd,J=15.0,9.7 Hz,2H), 7.50(br t,J=6.5 Hz,2H).

Example 12

Preparation of N,N'-bis[5-(3,4,5-trimethoxyphenyl)penta-(2E,4E)-dienoyl]-N,N'-dimethyl-1,4-bis(aminomethyl)cyclohexane:

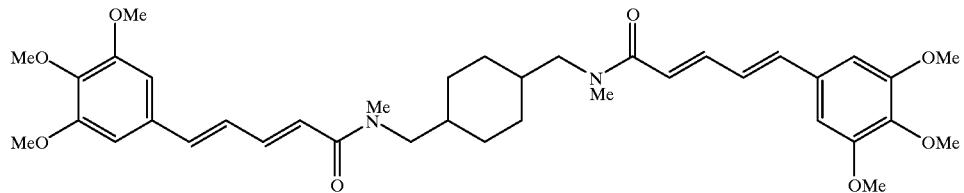

A solution of 100 mg (0.15 mmol) of N,N'-bis[5-(3,4,5-trimethoxyphenyl)-penta-(2E,4E)-dienoyl]-1,4-bis-(aminomethyl)cyclohexane synthesized by the process of Example 11 in anhydrous tetrahydrofuran (10 ml) was cooled in an ice bath under nitrogen. To the solution was added 0.20 ml (0.32 mmol) of a hexane solution (1.6 M) of n-butyllithium. The mixture was stirred for 10 minutes, and 0.20 ml (3.2 mmol) of methyl iodide was added to the mixture. The ice bath was removed, and the mixture was stirred for 12 hours at room temperature. Added to the reaction mixture was a 15% aqueous solution (5 ml) of ammonium chloride to conduct extraction with ethyl acetate. An organic layer was dried over anhydrous sodium sulfate and then concentrated under reduced pressure. The resultant crude oil (113 mg) was purified by column chromatography on silica gel, thereby obtaining 62 mg (yield: 60%) of the title compound as a pale yellow amorphous powder.

$^1$H-NMR (DMSO-$d_6$, 120° C.) δ: 1.30–1.50(m,8H), 1.75–1.90(m,2H), 2.98(s,6H), 3.30–3.40(m,4H), 3.72(s,6H), 3.82(s,12H), 6.55–6.85(m,4H), 6.81(s,4H), 6.97(dd,J=15.4, 10.6 Hz,2H), 7.20(dd,J=14.5,10.6 Hz,2H).

Example 13

Preparation of N,N'-bis[5-(3,4,5-trimethoxyphenyl)penta-(2E,4E)-dienoyl]-1,4-diaminocyclohexane:

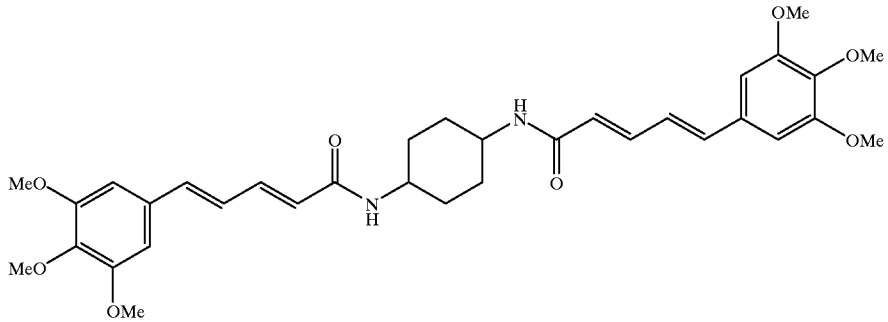

In accordance with the same process as in Example 1, 107 mg (yield: 18%) of the title compound was obtained as a colorless amorphous powder from 495 mg (2.2 mmol) of 5-(3,4,5-trimethoxyphenyl)penta-(2E,4E)-dienoic acid and 114 mg (1.0 mmol) of 1,4-diaminocyclohexane.

$^1$H-NMR (DMSO-$d_6$, 120° C.) δ: 1.02–1.41(m,4H), 1.79–1.96(m,4H), 3.54–3.80(m,2H), 3.72(s,6H), 3.82(s,12H), 6.11(d,J=14.9 Hz,2H), 6.78(d,J=15.6 Hz,2H), 6.81(s, 4H), 6.87(dd,J=15.6,9.5 Hz,2H), 7.15(dd,J=14.9,9.5 Hz,2H), 7.41(br d,J=6.8 Hz,2H).

Example 14

Preparation of cis-N,N'-bis[5-(3,4,5-trimethoxyphenyl) penta-(2E,4E)-dienoyl]-1,2-diaminocyclohexane:

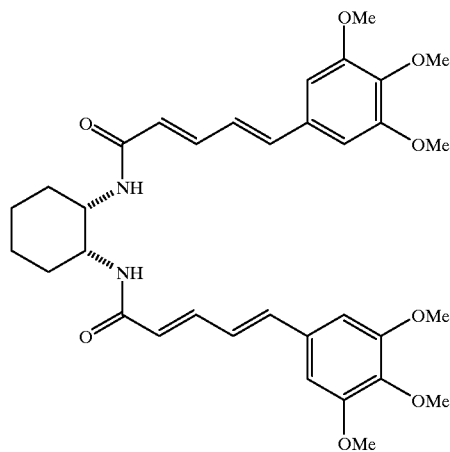

In accordance with the same process as in Example 1, 174 mg (yield: 87%) of the title compound was obtained as a colorless amorphous powder from 175 mg (0.66 mmol) of 5-(3,4,5-trimethoxyphenyl)penta-(2E,4E)-dienoic acid and 40 mg (0.33 mmol) of cis-1,2-diaminocyclohexane.

$^1$H-NMR (DMSO-$d_6$, 120° C.) δ: 1.33–1.52(m,2H), 1.54–1.81(m,6H), 3.76(s,6H), 3.84(s,12H), 4.03–4.16(m, 2H), 6.24(d,J=15.0 Hz,2H), 6.77–6.96(m,4H), 6.83(s,4H), 7.19(dd,J=15.0,8.7 Hz,2H), 7.29(br d,J=6.6 Hz,2H).

Example 15

Preparation of trans-N,N'-bis[5-(3,4,5-trimethoxyphenyl) penta-(2E,4E)-dienoyl]-1,2-diaminocyclohexane:

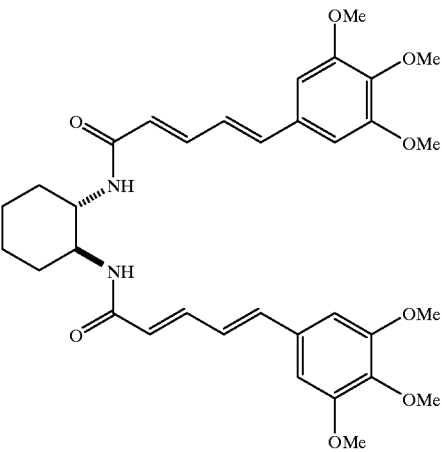

In accordance with the same process as in Example 1, 572 mg (yield: 94%) of the title compound was obtained as a colorless amorphous powder from 495 mg (2.2 mmol) of 5-(3,4,5-trimethoxyphenyl)penta-(2E,4E)-dienoic acid and 114 mg (1.0 mmol) of trans-1,2-diaminocyclohexane. The thus-obtained amorphous powder was recrystallized from methanol-ether-chloroform, thereby obtaining colorless needles.

Melting point: 254–257° C.

$^1$H-NMR (DMSO-$d_6$, 120° C.) δ: 1.22–1.40(m,4H), 1.64–1.74(m,2H), 1.89–2.02(m,2H), 3.62–3.71(m,2H), 3.72

(s,6H), 3.80(s,12H), 6.06(d,J=15.1 Hz,2H), 6.75(d,J=15.5 Hz,2H), 6.76(s,4H), 6.84(dd,J=15.5,9.8 Hz,2H), 7.13(dd,J=15.1,9.8 Hz,2H), 7.30–7.40(m,2H).

Example 16

Preparation of (1S,2S)-N,N'-bis[5-(3,4,5-trimethoxyphenyl)penta-(2E,4E)-dienoyl]-1,2-diaminocyclohexane:

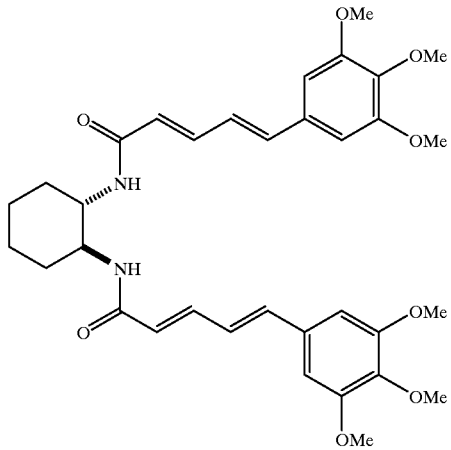

In accordance with the same process as in Example 1, 134 mg (yield: 65%) of the title compound was obtained as a colorless amorphous powder from 177 mg (0.67 mmol) of 5-(3,4,5-trimethoxyphenyl)penta-(2E,4E)-dienoic acid and 39 mg (0.34 mmol) of (1S,2S)-1,2-diaminocyclohexane. The thus-obtained amorphous powder was recrystallized from ethanol-ether, thereby obtaining colorless needles.

Melting point: 234–235° C.

Specific rotation: $[\alpha]^{23}_D = +240°$ (c 0.50, CHCl$_3$).

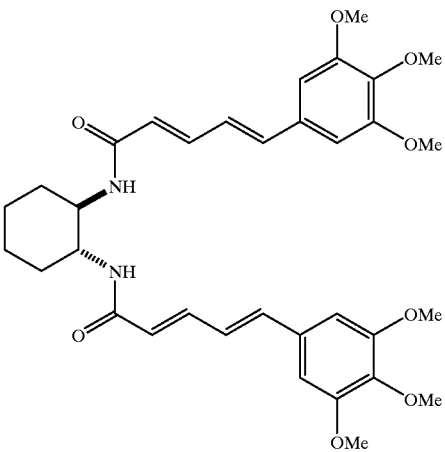

In accordance with the same process as in Example 1, 194 mg (yield: 97%) of the title compound was obtained as a colorless amorphous powder from 175 mg (0.66 mmol) of 5-(3,4,5-trimethoxyphenyl)penta-(2E,4E)-dienoic acid and 38 mg (0.33 mmol) of (1R,2R)-1,2-diaminocyclohexane. The thus-obtained amorphous powder was recrystallized from ethanol-ether, thereby obtaining colorless needles.

Melting point: 234–236° C.

Specific rotation: $[\alpha]^{23}_D = -240°$ (c 0.50, CHCl$_3$).

Example 18

Preparation of N,N-bis[N-[5-(3,4,5-trimethoxyphenyl)penta-(2E,4E)-dienoyl]-3-aminopropyl]methylamine:

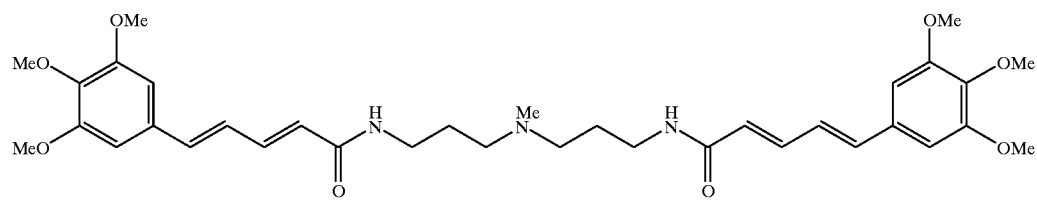

Example 17

Preparation of (1R,2R)-N,N'-bis[5-(3,4,5-trimethoxyphenyl)penta-(2E,4E)-dienoyl]-1,2-diaminocyclohexane:

In accordance with the same process as in Example 1, 341 mg (yield: 96%) of the title compound was obtained as a colorless amorphous powder from 295 mg (1.1 mmol) of 5-(3,4,5-trimethoxyphenyl)penta-(2E,4E)-dienoic acid and 81 mg (0.56 mmol) of N,N-bis(3-aminopropyl)methylamine.

¹H-NMR (DMSO-d₆, 120° C.) [mixture (7:1) of amide rotamers] δ: 1.61(tt,J=7.0,7.0 Hz,0.5H), 1.62(tt,J=7.0,7.0 Hz,3.5H), 2.16(s,0.4H), 2.17(s,2.6H), 2.36(t,J=7.0 Hz,0.5H), 2.37(t,J=7.0 Hz,3.5H), 3.19(dt,J=7.0,7.0 Hz,0.5H), 3.21(dt,J=7.0,7.0 Hz,3.5H), 3.72(s,5.2H), 3.72(s,0.8H), 3.81(s,10.5H), 3.82(s,1.5H), 6.11(d,J=15.0 Hz,0.2H), 6.12(d,J=15.0 Hz,1.8H), 6.77(d,J=15.5 Hz,2H), 6.79(s,3.5H), 6.80(s,0.5H), 6.87(dd,J=15.5,10.0 Hz,2H), 7.14(dd,J=15.0,10.0 Hz,0.2H), 7.15(dd,J=15.0,10.0 Hz,1.8H), 7.56(br t,J=7.0 Hz,2H).

Example 19

Preparation of 1,4-bis[N-[5-(3,4,5-trimethoxyphenyl)penta-(2E,4E)-dienoyl]-3-aminopropyl]piperazine:

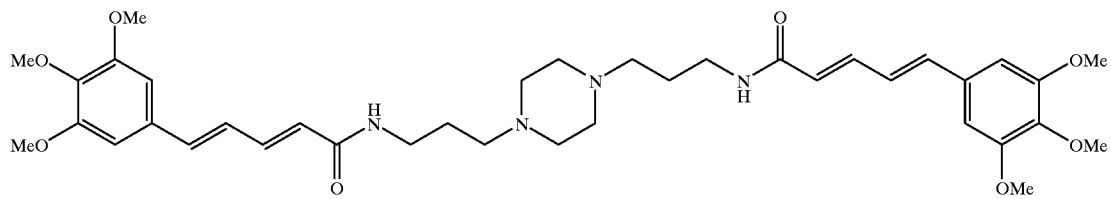

In accordance with the same process as in Example 1, 424 mg (yield: 49%) of the title compound was obtained as a colorless amorphous powder from 660 mg (2.5 mmol) of 5-(3,4,5-trimethoxyphenyl)penta-(2E,4E)-dienoic acid and 251 mg (1.3 mmol) of 1,4-bis(3-aminopropyl)piperazine.

¹H-NMR (DMSO-d₆, 120° C.) δ: 1.62(tt,J=6.9,6.9 Hz,4H), 2.34(t,J=6.9 Hz,4H), 2.41(s,8H), 3.19(dt,J=6.9,6.9 Hz,4H), 3.72(s,6H), 3.82(s,12H), 6.09(d,J=15.0 Hz,2H), 6.78(d,J=15.5 Hz,2H), 6.80(s,4H), 6.87(dd,J=15.5,9.6 Hz,2H), 7.14(dd,J=15.0,9.6 Hz,2H), 7.54(br t,J=6.9 Hz,2H).

Example 20

Preparation of 1,4-bis[N-ethyl-N-[5-(3,4,5-trimethoxyphenyl)penta-(2E,4E)-dienoyl]-3-aminopropyl]-piperazine:

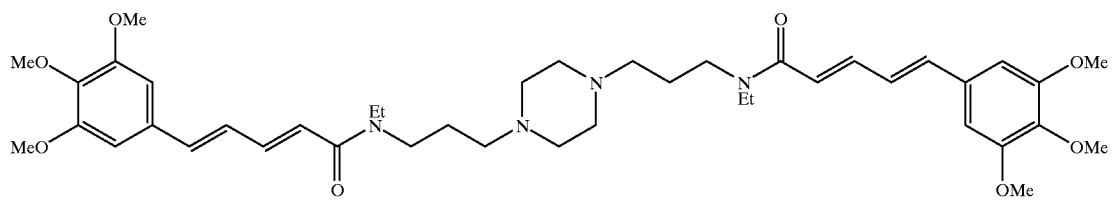

In accordance with the same process as in Example 1, 72 mg (yield: 36%) of the title compound was obtained as a pale yellow amorphous powder from 160 mg (0.61 mmol) of 5-(3,4,5-trimethoxyphenyl)penta-(2E,4E)-dienoic acid and 69 mg (0.27 mmol) of 1,4-bis(N-ethyl-3-aminopropyl) piperazine.

$^1$H-NMR (DMSO-$d_6$, 120° C.) δ: 1.13(t,J=7.1 Hz,6H), 1.69(tt,J=6.9,6.9 Hz,4H), 2.32(t,J=6.9 Hz,4H), 2.43(s,8H), 3.34–3.46(m,8H), 3.74(s,6H), 3.83(s,12H), 6.60(d,J=14.6 Hz,2H), 6.82(s,4H), 6.82(d,J=15.5 Hz,2H), 6.98(dd,J=15.5, 10.6 Hz,2H), 7.22(dd,J=14.6,10.6 Hz,2H).

Example 21

Preparation of 1,4-bis[N-benzyl-N-[5-(3,4,5-trimethoxyphenyl)penta-(2E,4E)-dienoyl]-3-aminopropyl] piperazine:

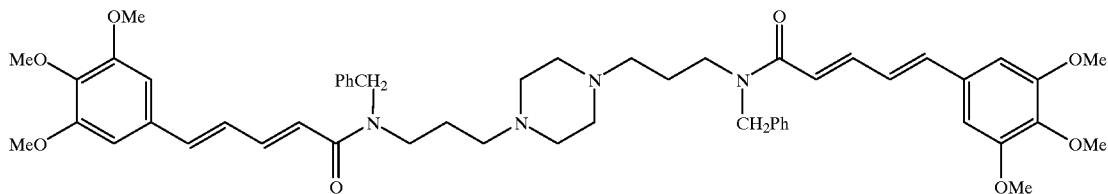

In accordance with the same process as in Example 4, crude crystals were obtained from 136 mg (0.51 mmol) of 5-(3,4,5-trimethoxyphenyl)penta-(2E,4E)-dienoic acid and 97 mg (0.26 mmol) of 1,4-bis(N-benzyl-3-aminopropyl) piperazine. The crude crystals were recrystallized from chloroform-hexane, thereby obtaining 121 mg (yield: 54%) of a pale yellow crystalline powder.

Melting point: 191–193° C.

$^1$H-NMR (DMSO-$d_6$, 120° C.) δ: 1.68(tt,J=7.0,7.0 Hz,4H), 2.28(t,J=7.0 Hz,4H), 2.37(s,8H), 3.41(br t,J=7.0 Hz,4H), 3.75(s,6H), 3.84(s,12H), 4.66(s,4H), 6.67(d,J=14.7 Hz,2H), 6.83(s,4H), 6.86(d,J=15.6 Hz,2H), 6.98(dd,J=15.6, 10.3 Hz,2H), 7.22–7.38(m,12H).

Example 22

Preparation of N,N'-bis[5-(3,4,5-trimethoxyphenyl)penta-(2E,4E)-dienoyl]-1,4-bis(aminomethyl)benzene:

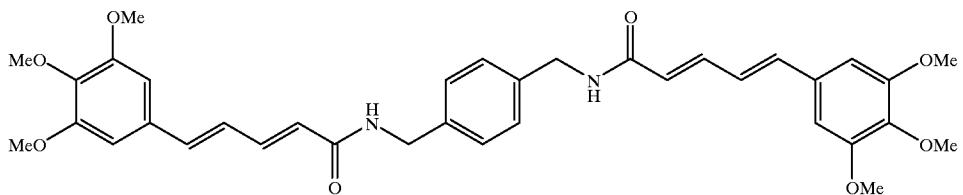

In accordance with the same process as in Example 4, crude crystals were obtained from 318 mg (1.2 mmol) of 5-(3,4,5-trimethoxyphenyl)penta-(2E,4E)-dienoic acid and 68 mg (0.50 mmol) of 1,4-bis(aminomethyl)benzene. The thus-obtained crude crystals were recrystallized from methanol-chloroform-hexane, thereby obtaining 230 mg (yield: 73%) of the title compound as colorless fine needles.

Melting point: 228–230° C.

$^1$H-NMR (DMSO-$d_6$, 120° C.) δ: 3.72(s,6H), 3.82(s,12H), 4.35(d,J=5.9 Hz,4H), 6.17(d,J=15.0 Hz,2H), 6.79(d, J=15.5 Hz,2H), 6.81(s,4H), 6.89(dd,J=15.5,9.5 Hz,2H), 7.20 (dd,J=15.0,9.5 Hz,2H), 7.23(s,4H), 8.03(br t,J=5.9 Hz,2H).

Example 23

Preparation of N,N'-bis[5-(3,4,5-trimethoxyphenyl)penta-(2E,4E)-dienoyl]-N,N'-dimethyl-1,4-bis(aminomethyl)benzene:

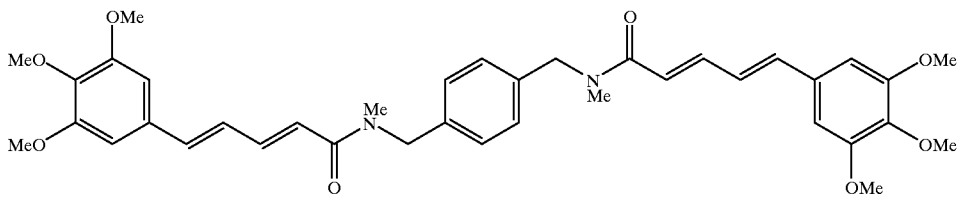

In accordance with the same process as in Example 12, 117 mg (yield: 62%) of the title compound was obtained as a colorless amorphous powder from 180 mg (0.29 mmol) of N,N'-bis[5-(3,4,5-trimethoxyphenyl)penta-(2E,4E)-dienoyl]-1,4-bis(aminomethyl)benzene synthesized by the process of Example 22 and 0.45 ml (7.2 mmol) of methyl iodide. The thus-obtained amorphous powder was recrystallized from chloroform-hexane to obtain a colorless crystalline powder.

Melting point: 223–226° C.

$^1$H-NMR (DMSO-$d_6$, 120° C.) δ: 2.96(s,6H), 3.72(s,6H), 3.81(s,12H), 4.61(s,4H), 6.65(d,J=14.7 Hz,2H), 6.80(s,4H), 6.83(d,J=15.1 Hz,2H), 6.97(dd,J=15.1,10.5 Hz,2H), 7.22(s, 4H), 7.27(dd,J=14.7,10.5 Hz,2H).

Example 24

Preparation of N,N'-bis[5-(3,4,5-trimethoxyphenyl)penta-(2E,4E)-dienoyl]-1,3-bis(aminomethyl)benzene:

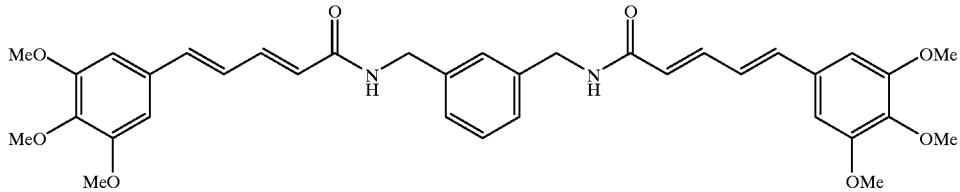

In accordance with the same process as in Example 1, crude crystals were obtained from 180 mg (0.68 mmol) of 5-(3,4,5-trimethoxyphenyl)penta-(2E,4E)-dienoic acid and 0.045 ml (0.34 mmol) of 1,3-bis(aminomethyl)benzene. The thus-obtained crude crystals were recrystallized from methanol-chloroform-hexane, thereby obtaining 127 mg (yield: 59%) of the title compound as colorless flakes.

Melting point: 194–195° C.

$^1$H-NMR (DMSO-$d_6$, 120° C.) δ: 3.72(s,6H), 3.81(s,12H), 4.36(d,J=5.9 Hz,4H), 6.18(d,J=15.2 Hz,2H), 6.79(d, J=15.5 Hz,2H), 6.81(s,4H), 6.89(dd,J=15.5,9.8 Hz,2H), 7.13–7.28(m,4H), 7.20(dd,J=15.2,9.8 Hz,2H), 8.06(br t,J= 5.9 Hz,2H).

Example 25

Preparation of 2,6-bis[N-methyl-N-[5-(3,4,5-trimethoxyphenyl)penta-(2E,4E)-dienoyl]aminomethyl]pyridine:

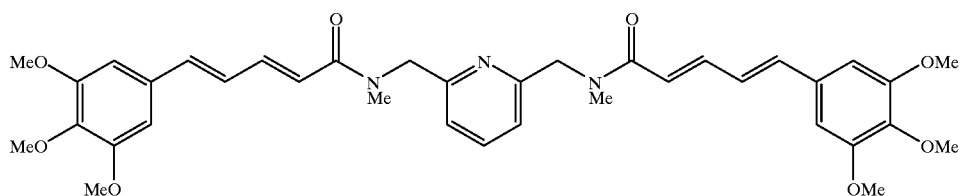

In accordance with the same process as in Example 1, 103 mg (yield: 22%) of the title compound was obtained as a pale yellow amorphous powder from 371 mg (1.4 mmol) of 5-(3,4,5-trimethoxyphenyl)penta-(2E,4E)-dienoic acid and 115 mg (0.70 mmol) of 2,6-bis(methylaminomethyl)pyridine.

$^1$H-NMR (DMSO-$d_6$, 120° C.) δ: 3.05(s,6H), 3.72(s,6H), 3.81(s,12H), 4.68(s,4H), 6.66(d,J=14.7 Hz,2H), 6.79(d,J=

15.5 Hz,2H), 6.80(s,4H), 6.96(dd,J=15.5,10.6 Hz,2H), 7.15 (d,J=7.8 Hz,2H), 7.24(dd,J=14.7,10.6 Hz,2H), 7.73(t,J=7.8 Hz,1H).

Example 26
Preparation of N,N'-bis[5-(3,4,5-trimethoxyphenyl)penta-(2E,4E)-dienoyl]-1,2-diaminobenzene:

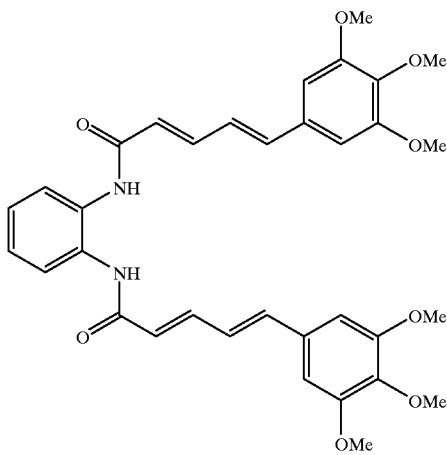

In accordance with the same process as in Example 4, 378 mg (yield: 97%) of the title compound was obtained as a colorless crystalline powder from 400 mg (1.5 mmol) of 5-(3,4,5-trimethoxyphenyl)penta-(2E,4E)-dienoic acid and 70 mg (0.65 mmol) of 1,2-diaminobenzene.

Melting point: 226–229° C.

$^1$H-NMR (DMSO-$d_6$, 120° C.) δ: 3.73(s,6H), 3.82(s, 12H), 6.33(d,J=15.1 Hz,2H), 6.84(s,4H), 6.89(d,J=15.5 Hz,2H), 6.99(dd,J=15.5,9.7 Hz,2H), 7.13–7.19(m,2H), 7.35 (dd,J=15.1,9.7 Hz,2H), 7.61–7.67(m,2H), 9.32(br s,2H).

Example 27
Preparation of N,N'-bis[5-(3,4,5-trimethoxyphenyl)penta-(2E,4E)-dienoyl]-N,N'-dimethyl-1,2-diaminobenzene:

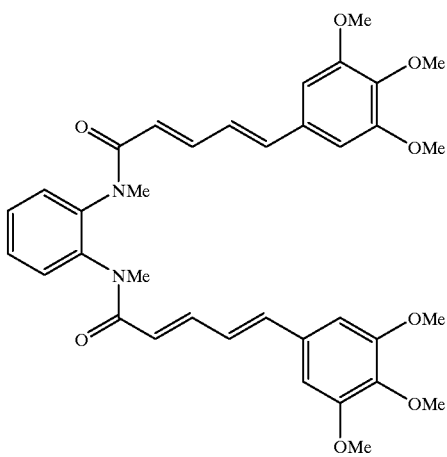

In accordance with the same process as in Example 12, 154 mg (yield: 88%) of the title compound was obtained as a colorless amorphous powder from 166 mg (0.28 mmol) of N,N'-bis[5-(3,4,5-trimethoxyphenyl)penta-(2E,4E)-dienoyl]-1,2-diaminobenzene synthesized by the process of Example 26 and 0.40 ml (6.4 mmol) of methyl iodide.

$^1$H-NMR (DMSO-$d_6$, 120° C.) δ: 3.14(s,6H), 3.68(s,6H), 3.74(s,12H), 6.02(br-d,J=14.9 Hz,2H), 6.69–6.87(m,4H), 6.72(s,4H), 7.21(dd,J=14.9,7.9 Hz,1H), 7.22(dd,J=14.9,7.9 Hz,1H), 7.34–7.41(m,2H), 7.44–7.51(m,2H).

Example 28
Preparation of N,N'-bis[5-(3,4,5-trimethoxyphenyl)penta-(2E,4E)-dienoyl]-N,N'-dibenzyl-1,2-diaminobenzene:

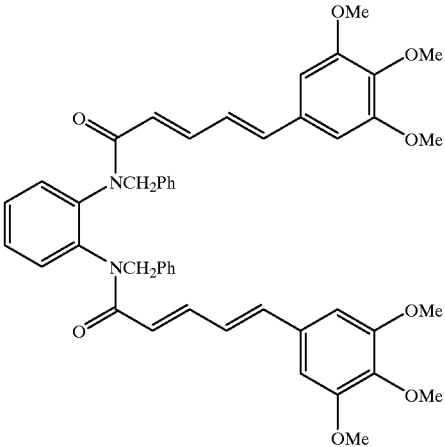

In accordance with the same process as in Example 12, 147 mg (yield: 67%) of the title compound was obtained as a pale yellow amorphous powder from 168 mg (0.28 mmol) of N,N'-bis[5-(3,4,5-trimethoxyphenyl)penta-(2E,4E)-dienoyl]-1,2-diaminobenzene synthesized by the process of Example 26 and 0.65 ml (5.5 mmol) of benzyl bromide.

$^1$H-NMR (DMSO-$d_6$, 120° C.) (mixture of amide rotamers) δ: 3.64–3.78(m,18H), 3.60–5.30(br,4H), 6.03(br d,J=14.8 Hz,2H), 6.69–6.85(m,8H), 7.00–7.08(m,2H), 7.13–7.41(m,14H).

Example 29
Preparation of N,N'-bis[5-(3,4,5-trimethoxyphenyl)penta-(2E,4E)-dienoyl]-2,3-diaminophenol:

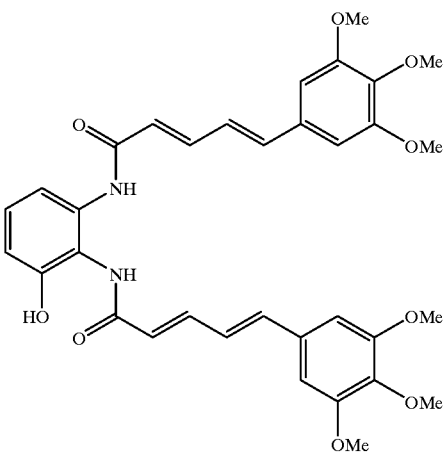

A solution of 286 mg (1.1 mmol) of 5-(3,4,5-trimethoxyphenyl)penta-(2E,4E)-dienoic acid in anhydrous dimethylformamide-methylene chloride (0.1 ml–10 ml) was cooled in an ice bath. To the solution was added 0.12 ml (1.3 mmol) of oxalyl chloride with stirring. The ice bath was removed, and the mixture was stirred for 30 minutes at room temperature. The reaction mixture was concentrated under reduced pressure to obtain crude crystals of 5-(3,4,5-trimethoxyphenyl)penta-(2E,4E)-dienoyl chloride.

Added to a solution of 44 mg (0.35 mmol) of 2,3-diaminophenol in anhydrous methylene chloride was 2 ml (25 mmol) of pyridine, and the resultant mixture was cooled in an ice bath. A solution of 5-(3,4,5-trimethoxyphenyl) penta-(2E,4E)-dienoyl chloride in methylene chloride (5 ml) was added dropwise to the mixture over about 5 minutes. After completion of the addition, the resultant mixture was stirred for an additional 1 hour, and water was then added to conduct extraction with chloroform. An organic layer was dried over anhydrous sodium sulfate and then concentrated under reduced pressure. The resultant crude oil (515 mg) was purified by column chromatography on silica gel, thereby obtaining 258 mg (yield: 85%) of crude crystals of N,N',O-tri[5-(3,4,5-trimethoxyphenyl)penta-(2E,4E)-dienoyl]-2,3-diaminophenol as a pale brown amorphous powder.

A solution of 196 mg (0.23 mmol) of N,N',O-tri[5-(3,4,5-trimethoxyphenyl)penta-(2E,4E)-dienoyl]-2,3-diaminophenol synthesized by the process described above in anhydrous methanol-tetrahydrofuran (3 ml–3 ml) was cooled in an ice bath. To the solution was added 19 mg (0.14 mmol) of potassium carbonate. The ice bath was removed, and the mixture was stirred for 1 hour at room temperature. Added to the reaction mixture were 0.5 ml of 1N hydrochloric acid and 5 ml of a saturated saline solution to conduct extraction with chloroform. An organic layer was dried over anhydrous sodium sulfate and then concentrated under reduced pressure. The resultant crude oil (515 mg) was purified by column chromatography on silica gel, thereby obtaining 126 mg (yield: 90%) of crude crystals of the title compound. The crude crystals thus obtained were recrystallized from ethanol-ether, thereby obtaining a pale yellow crystalline powder.

Melting point: 209–210° C.

$^1$H-NMR (DMSO-$d_6$, 120° C.) δ: 3.72(s,3H), 3.73(s,3H), 3.81(s,6H), 3.81(s,6H), 6.29(d,J=15.1 Hz,1H), 6.40(d,J=15.1 Hz,1H), 6.74(dd,J=8.2,1.5 Hz,1H), 6.83(s,2H), 6.84(s,2H), 6.86(d,J=15.8 Hz,1H), 6.90(d,J=15.8 Hz,1H), 6.97(dd,J=15.8,10.0 Hz,1H), 6.99(dd,J=15.8,10.0 Hz,1H), 7.07(dd,J=8.2,8.2 Hz,1H), 7.27(dd,J=8.2,1.5 Hz,1H), 7.31(dd,J=15.1,10.0 Hz,1H) 7.36(dd,J=15.1,10.0 Hz,1H), 9.08(br s,1H), 9.10(br s,2H).

Example 30

Preparation of methyl N,N'-bis[5-(3,4,5-trimethoxyphenyl)penta-(2E,4E)-dienoyl]-3,4-diaminobenzoate:

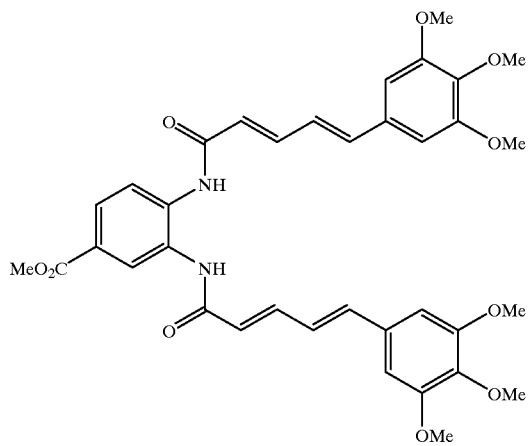

In accordance with the same process as in Example 4, crude crystals were obtained from 389 mg (1.5 mmol) of 5-(3,4,5-trimethoxyphenyl)penta-(2E,4E)-dienoic acid and 107 mg (0.65 mmol) of methyl 3,4-diaminobenzoate. The crude crystals were recrystallized from ethanol-ether, thereby obtaining 305 mg (yield: 72%) of the title compound as a pale yellow crystalline powder.

Melting point: at least 250° C.

$^1$H-NMR (DMSO-$d_6$, 120° C.) δ: 3.73(s,3H), 3.73(s,3H), 3.82(s,6H), 3.83(s,6H), 3.86(s,3H), 6.36(d,J=15.0 Hz,1H), 6.37(d,J=15.0 Hz,1H), 6.85(s,2H), 6.86(s,2H), 6.91(d,J=15.5 Hz,2H), 7.00(dd,J=15.5,9.5 Hz,2H), 7.38(dd,J=15.0,9.5 Hz,2H), 7.75(dd,J=8.6,2.0 Hz,1H), 7.92(d,J=8.6 Hz,1H), 8.24(d,J=2.0 Hz,1H), 9.48(br s,1H), 9.50(br s,1H).

Example 31

Preparation of N,N'-bis[5-(3,4,5-trimethoxyphenyl)penta-(2E,4E)-dienoyl]-3,4-diaminobenzoic acid:

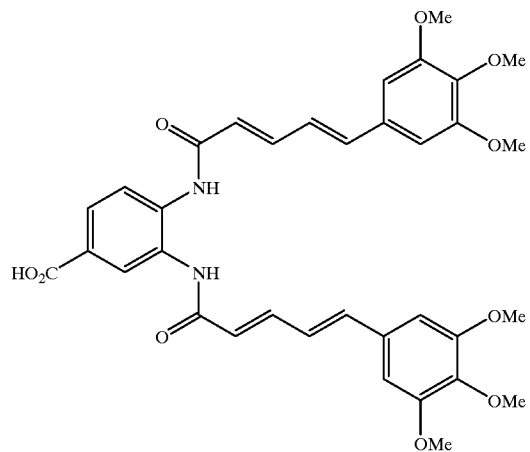

In accordance with the same process as in Example 10, crude crystals were obtained from 153 mg (0.23 mmol) of methyl N,N'-bis[5-(3,4,5-trimethoxyphenyl)penta-(2E,4E)-dienoyl]-3,4-diaminobenzoate synthesized by the process of Example 30. The crude crystals were recrystallized from ethanol-ether, thereby obtaining 141 mg (yield: 94%) of the title compound as a pale yellow crystalline powder.

Melting point: 202–205° C.

$^1$H-NMR (DMSO-$d_6$, 120° C.) (no OH proton of the carboxyl group was observed) δ: 3.73(s,6H), 3.82(s,6H), 3.82(s,6H), 6.36(d,J=14.9 Hz,1H), 6.36(d,J=14.9 Hz,1H), 6.85(s,2H), 6.86(s,2H), 6.91(d,J=15.5 Hz,2H), 7.00(dd,J=15.5,9.5 Hz,2H), 7.38(dd,J=14.9,9.5 Hz,2H), 7.74(dd,J=8.4,2.0 Hz,1H), 7.88(d,J=8.4 Hz,1H), 8.21(d,J=2.0 Hz,1H), 9.47 (br s,2H).

Example 32

Preparation of N,N'-bis[5-(3,4,5-trimethoxyphenyl)penta-(2E,4E)-dienoyl]-1,2-diamino-4-methoxybenzene:

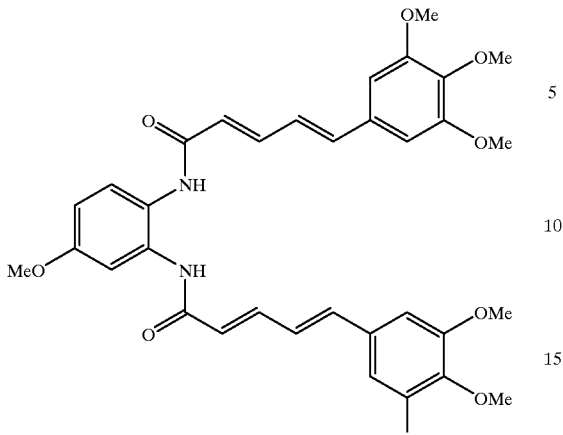

In accordance with the same process as in Example 4, crude crystals were obtained from 171 mg (0.65 mmol) of 5-(3,4,5-trimethoxyphenyl)penta-(2E,4E)-dienoic acid and 65 mg (0.31 mmol) of 1,2-diamino-4-methoxybenzene dihydrochloride. The crude crystals were recrystallized from ethanol-ether, thereby obtaining 133 mg (yield: 68%) of the title compound as a pale yellow crystalline powder.

Melting point: 231–233° C.

$^1$H-NMR (DMSO-$d_6$, 120° C.) δ: 3.73(s,6H), 3.77(s,3H), 3.82(s,6H), 3.82(s,6H), 6.30(d,J=15.0 Hz,1H), 6.31(d,J=15.0 Hz,1H), 6.75(dd,J=8.8,2.8 Hz,1H), 6.84(s,4H), 6.87(d, J=15.4 Hz,1H), 6.88(d,J=15.4 Hz,1H), 6.98(dd,J=15.4,9.9 Hz,1H), 6.99(dd,J=15.4,9.9 Hz,1H), 7.33(dd,J=15.0,9.9 Hz,1H), 7.34(dd,J=15.0,9.9 Hz,1H), 7.38(d,J=2.8 Hz,1H), 7.43(d,J=8.8 Hz,1H), 9.18(br s,1H), 9.26(br s,1H).

In accordance with the same process as in Example 4, crude crystals were obtained from 623 mg (2.2 mmol) of 5-(3,4,5-trimethoxyphenyl)penta-(2E,4E)-dienoic acid and 153 mg (1.0 mmol) of 1,2-diamino-4-nitrobenzene dihydrochloride. The crude crystals were recrystallized from ethyl acetate-chloroform-hexane, thereby obtaining 492 mg (yield: 76%) of the title compound as a pale yellow crystalline powder.

Melting point: 237–239° C.

$^1$H-NMR (DMSO-$d_6$, 120° C.) δ: 3.73(s,6H), 3.83(s,6H), 3.83(s,6H), 6.38(d,J=14.9 Hz,1H), 6.41(d,J=14.9 Hz,1H), 6.86(s,2H), 6.87(s,2H), 6.94(d,J=15.5 Hz,2H), 7.02(dd,J=15.5,8.4 Hz,2H), 7.41(br dd,J=14.9,8.4 Hz,2H), 8.00(dd,J=9.0,2.4 Hz,1H), 8.09(d,J=9.0 Hz,1H), 8.60(d,J=2.4 Hz,1H), 9.60(br s,1H), 9.64(br s,1H).

Example 33

Preparation of N,N'-bis[5-(3,4,5-trimethoxyphenyl)penta-(2E,4E)-dienoyl]-1,2-diamino-4-nitrobenzene:

Example 34

Preparation of N,N'-bis[5-(3,4,5-trimethoxyphenyl)penta-(2E,4E)-dienoyl]-1,4-diaminobenzene:

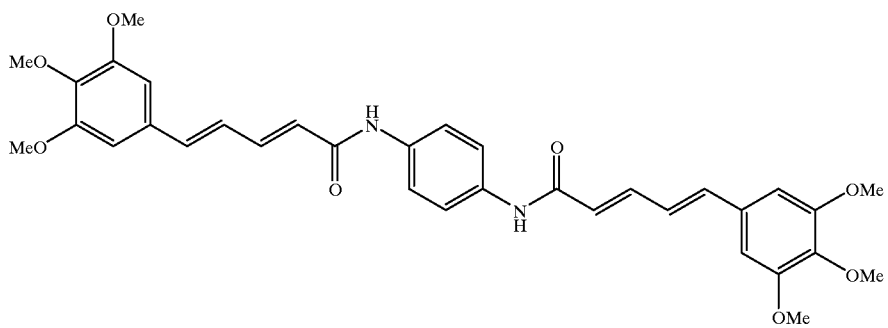

In accordance with the same process as in Example 4, crude crystals were obtained from 350 mg (1.3 mmol) of 5-(3,4,5-trimethoxyphenyl)penta-(2E,4E)-dienoic acid and 121 mg (0.67 mmol) of 1,4-diaminobenzene dihydrochloride. The crude crystals were recrystallized from dimethylformamide-ether, thereby obtaining 135 mg (yield: 34%) of the title compound as a yellow crystalline powder.

Melting point: 270° C.

$^1$H-NMR (DMSO-$d_6$, 120° C.) δ: 3.73(s,6H), 3.83(s,12H), 6.31(d,J=15.1 Hz,2H), 6.85(s,4H), 6.87(br d,J=15.5 Hz,2H), 6.95(dd,J=15.5,9.2 Hz,2H), 7.32(ddd,J=15.1,9.2,0.7 Hz,2H), 7.58(s,4H), 9.58(br s,2H).

Example 35
Preparation of methyl N,N'-bis[5-(3,4,5-trimethoxyphenyl)penta-(2E,4E)-dienoyl]-3,5-diaminobenzoate:

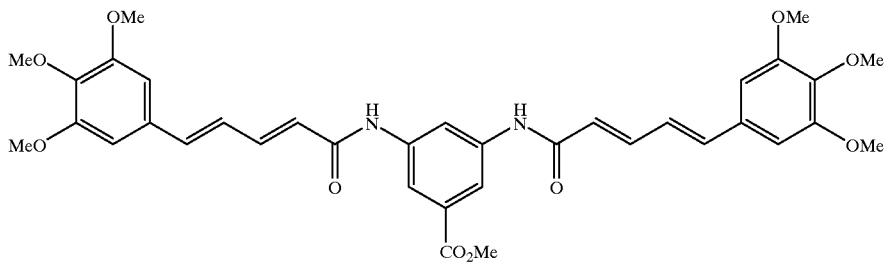

In accordance with the same process as in Example 4, crude crystals were obtained from 340 mg (1.3 mmol) of 5-(3,4,5-trimethoxyphenyl)penta-(2E,4E)-dienoic acid and 105 mg (0.64 mmol) of methyl 3,5-diaminobenzoate. The crude crystals were recrystallized from chloroform-ether, thereby obtaining 301 mg (yield: 72%) of the title compound as a pale yellow crystalline powder.

Melting point: 158–162° C.

$^1$H-NMR (DMSO-$d_6$, 120° C.) δ: 3.74(s,6H), 3.84(s,12H), 3.87(s,3H), 6.34(d,J=14.9 Hz,2H), 6.86(s,4H), 6.90(br d,J=15.4 Hz,2H), 6.98(dd,J=15.4,9.0 Hz,2H), 7.36(ddd,J=14.9,9.0,1.0 Hz,2H), 7.99(d,J=2.1 Hz,2H), 8.33(t,J=2.1 Hz,1H), 9.91(br s,2H).

Example 36
Preparation of N,N'-bis[5-(3,4,5-trimethoxyphenyl)penta-(2E,4E)-dienoyl]-3,5-diaminobenzoic acid:

In accordance with the same process as in Example 10, crude crystals were obtained from 161 mg (0.24 mmol) of methyl N,N'-bis[5-(3,4,5-trimethoxyphenyl)penta-(2E,4E)-dienoyl]-3,5-diaminobenzoate synthesized by the process of Example 35. The crude crystals were recrystallized from ethanol-ether, thereby obtaining 156 mg (yield: 99%) of the title compound as a pale yellow crystalline powder.

Melting point: 250° C.

$^1$H-NMR (DMSO-$d_6$, 120° C.) (no OH proton of the carboxyl group was observed) δ: 3.74(s,6H), 3.84(s,12H), 6.36(d,J=14.9 Hz,2H), 6.86(s,4H), 6.89(br d,J=15.4 Hz,2H), 6.98(dd,J=15.4,9.2 Hz,2H), 7.36(ddd,J=14.9,9.2,1.0 Hz,2H), 7.97(d,J=2.0 Hz,2H), 8.30(t,J=2.0 Hz,1H), 9.90(br s,2H).

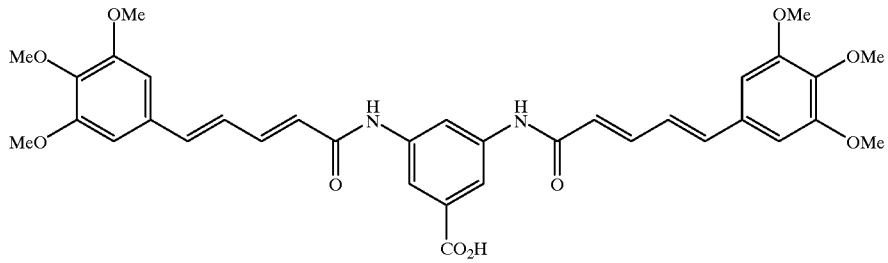

Example 37

Preparation of N,N'-bis[5-(3,4,5-trimethoxyphenyl)penta-(2E,4E)-dienoyl]-1,3-diamino-5-(N,N-dimethylaminomethyl)benzene:

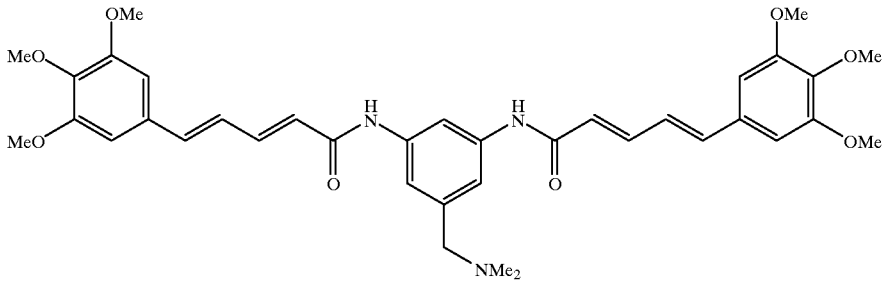

In accordance with the same process as in Example 4, 128 mg (yield: 63%) of the title compound was obtained as a pale yellow amorphous powder from 152 mg (0.58 mmol) of 5-(3,4,5-trimethoxyphenyl)penta-(2E,4E)-dienoic acid and 51 mg (0.31 mmol) of 1,3-diamino-5-(N,N-dimethylaminomethyl)benzene.

$^1$H-NMR (DMSO-$d_6$, 120° C.) δ: 2.24(s,6H), 3.41(s,2H), 3.73(s,6H), 3.83(s,12H), 6.34(d,J=14.9 Hz,2H), 6.86(s,4H), 6.87(br d,J=15.4 Hz,2H), 6.96(dd,J=15.4,9.3 Hz,2H), 7.32 (ddd,J=14.9,9.3,1.0 Hz,2H), 7.33(d,J=2.0 Hz,2H), 7.95(t,J= 2.0 Hz,1H), 9.65(br s,2H).

Example 38

Preparation of 2,3-bis[5-(3,4,5-trimethoxyphenyl)penta-(2E,4E)-dienoylamino]pyridine:

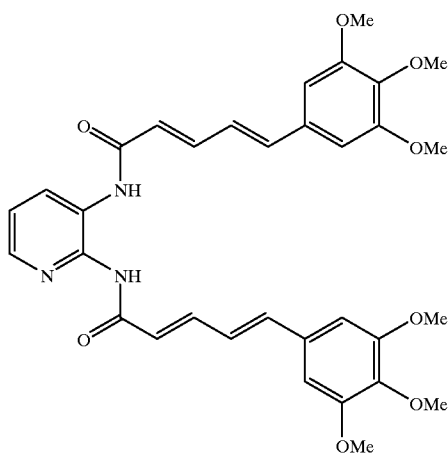

In accordance with the same process as in Example 4, 255 mg (yield: 87%) of the title compound was obtained as a yellow amorphous powder from 302 mg (1.1 mmol) of 5-(3,4,5-trimethoxyphenyl)penta-(2E,4E)-dienoic acid and 53 mg (0.49 mmol) of 2,3-diaminopyridine.

$^1$H-NMR (DMSO-$d_6$, 120° C.) (one amide NH proton was not observed) δ: 3.73(s,3H), 3.74(s,3H), 3.82(s,6H), 3.83(s, 6H), 6.26(d,J=15.0 Hz,1H), 6.52(d,J=15.0 Hz,1H), 6.85(s, 2H), 6.86(s,2H), 6.91–7.06(m,4H), 7.26(dd,J=8.1,4.6 Hz,1H), 7.33(dd,J=15.0,10.1 Hz,1H), 7.46(ddd,J=15.0,8.9, 1.3 Hz,1H), 8.19(dd,J=4.6,1.6 Hz,1H), 8.31(dd,J=8.1,1.6 Hz,1H), 9.53(br s,1H).

Example 39

Preparation of 3,4-bis[5-(3,4,5-trimethoxyphenyl)penta-(2E,4E)-dienoylamino]pyridine:

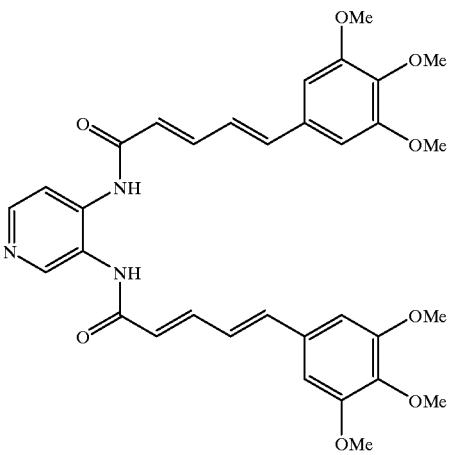

In accordance with the same process as in Example 4, 88 mg (yield: 34%) of crude crystals of the title compound were obtained from 263 mg (1.0 mmol) of 5-(3,4,5-trimethoxyphenyl)penta-(2E,4E)-dienoic acid and 47 mg (0.43 mmol) of 3,4-diaminopyridine. The crude crystals were recrystallized from ethanol-ether, thereby obtaining a yellow crystalline powder.

Melting point: 174–176° C.

$^1$H-NMR (DMSO-$d_6$, 120° C.) δ: 3.73(s,3H), 3.74(s,3H), 3.82(s,6H), 3.83(s,6H), 6.36(d,J=15.0 Hz,1H), 6.37(d,J= 15.0 Hz,1H), 6.85(s,2H), 6.86(s,2H), 6.88–7.06(m,4H), 7.39 (ddd,J=15.0,7.8,1.2 Hz,1H), 7.39(dd,J=15.0,9.3 Hz,1H), 7.94(d,J=5.5 Hz,1H), 8.29(d,J=5.5 Hz,1H), 8.65(s,1H), 9.48 (br s,2H).

Example 40
Preparation of 2,6-bis[5-(3,4,5-trimethoxyphenyl)penta-(2E,4E)-dienoylamino]pyridine:

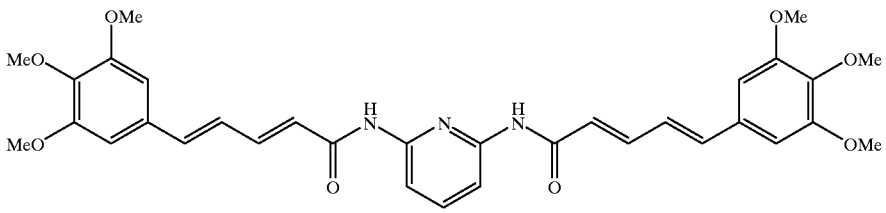

In accordance with the same process as in Example 4, 250 mg (yield: 85%) of crude crystals of the title compound were obtained from 302 mg (1.1 mmol) of 5-(3,4,5-trimethoxyphenyl)penta-(2E,4E)-dienoic acid and 53 mg (0.49 mmol) of 2,6-diaminopyridine. The crude crystals were recrystallized from chloroform-ether, thereby obtaining a yellow crystalline powder.

Melting point: 203–207° C.
$^1$H-NMR (DMSO-$d_6$, 120° C.) δ: 3.74(s,6H), 3.83(s,12H), 6.51(d,J=15.1 Hz,2H), 6.86(s,4H), 6.88–7.02(m,4H), 7.38(ddd,J=15.1,7.6,2.5 Hz,2H), 7.67–7.82(m,3H), 9.68(br s,2H).

Example 41
Preparation of N,N'-bis[5-(2,6-dimethoxyphenyl)penta-(2E,4E)-dienoyl]-1,4-bis(aminomethyl)benzene:

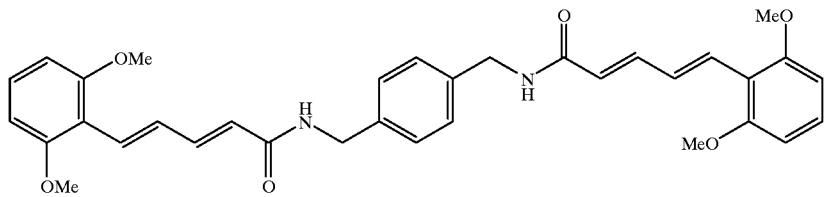

In accordance with the same process as in Example 1, 128 mg (yield: 68%) of the title compound was obtained as a colorless amorphous powder from 156 mg (0.67 mmol) of 5-(2,6-dimethoxyphenyl)penta-(2E,4E)-dienoic acid and 45 mg (0.33 mmol) of 1,4-bis(aminomethyl)benzene.

$^1$H-NMR (DMSO-$d_6$, 120° C.) (mixture of amide rotamers) δ: 3.83(s,12H), 4.34(d,J=5.9 Hz,4H), 6.01–6.16 (m,2H), 6.66(d,J=8.3 Hz,4H), 7.01–7.25(m,6H), 7.19(t,J=8.3 Hz,2H), 7.23(s,4H), 7.94(br t,J=5.9 Hz,2H).

Example 42
Preparation of N,N'-bis[5-(4-tert-butyl-2-methoxyphenyl)penta-(2E,4E)-dienoyl]-1,4-bis(aminomethyl)benzene:

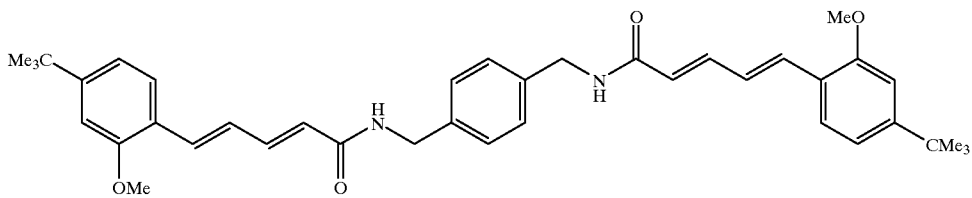

In accordance with the same process as in Example 1, crude crystals were obtained from 152 mg (0.59 mmol) of 5-(4-tert-butyl-2-methoxyphenyl)penta-(2E,4E)-dienoic acid and 40 mg (0.29 mmol) of 1,4-bis(aminomethyl)benzene. The crude crystals were recrystallized from chloroform-hexane, thereby obtaining 117 mg (yield: 65%) of the title compound as a colorless crystalline powder.

Melting point: 237–239° C.
$^1$H-NMR (DMSO-$d_6$, 120° C.) δ: 1.30(s,18H), 3.84(s,6H), 4.34(d,J=6.1 Hz,4H), 6.13(br d,J=15.0 Hz,2H), 6.89 (ddd,J=15.6,10.5,0.5 Hz,2H), 6.93–7.00(m,4H), 7.05(d,J=15.6 Hz,2H), 7.20(dd,J=15.0,10.5 Hz,2H), 7.23(s,4H), 7.42 (d,J=7.8 Hz,2H), 7.98(br t,J=6.1 Hz,2H).

Referential Example 1:
Preparation of trans-1-benzyl-3,4-bis(aminomethyl)pyrrolidine:

A solution of 291 mg (3.7 mmol) of fumaronitrile and 1.06 g (4.5 mmol) of N-benzyl-N-(methoxymethyl) trimethylsilylmethylamine in anhydrous methylene chloride (7.5 ml) was cooled in an ice bath. To the solution was added 0.37 ml (0.37 mmol) of a 1 M solution of trifluoroacetic acid in methylene chloride. The ice bath was removed, and the mixture was stirred for 4 hours at room temperature. The reaction mixture was washed with a saturated solution of a sodium hydrogencarbonate and a saturated saline solution, dried over anhydrous sodium sulfate, and then concentrated under reduced pressure, thereby obtaining 789 mg of an oil containing trans-1-benzyl-3,4-dicyanopyrrolidine[(1)]. To a solution of 789 mg of the oil thus obtained in ethanol-chloroform (10:1, 22 ml) was added 54.6 mg of platinum oxide, and the resultant mixture was stirred for 3 days at room temperature under hydrogen. The catalyst was removed by suction filtration through Celite, and the filtrate was concentrated under reduced pressure. To a solution of the residue in water-methanol was added 1.5 g (11 mmol) of potassium carbonate. The mixture was stirred and then concentrated again under reduced pressure. The resultant residue was purified by column chromatography on alumina, thereby obtaining 403 mg (yield: 49%) of the title compound as a colorless oil.

(1) Terao, Y.; Kotaki, H.; Imai, N.; Achiwa, K., Chem. Pharm. Bull., 1985, 33, 2762–2766.

Example 43
Preparation of trans-1-benzyl-3,4-bis[5-(3,4,5-trimethoxyphenyl)penta-(2E,4E)-dienoylaminomethyl]pyrrolidine:

on silica gel to obtain 256 mg (yield: 44%) of trans-1-benzyl-3,4-bis(tert-butoxycarbonylaminomethyl)pyrrolidine as a colorless oil.

To a solution of 203 mg (0.49 mmol) of trans-1-benzyl-3,4-bis(tert-butoxycarbonyl-aminomethyl)pyrrolidine thus obtained in methanol (5 ml) were added 50 mg of 10% palladium on carbon and 0.25 ml (6.6 mmol) of formic acid, and the mixture was stirred for 4 hours at room temperature. The catalyst was removed from the reaction mixture by suction filtration through Celite, and the filtrate was concentrated under reduced pressure. The resultant crude oil was purified by column chromatography on silica gel, thereby obtaining 165 mg (quantitative) of trans-3,4-bis(tert-butoxycarbonylaminomethyl)pyrrolidine as a colorless oil.

To a solution of 145 mg (0.44 mmol) of trans-3,4-bis(tert-butoxycarbonylaminomethyl)pyrrolidine synthesized by the

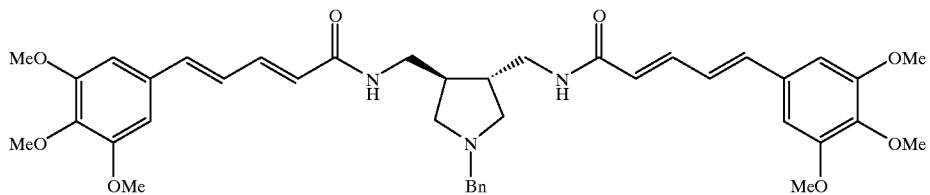

In accordance with the same process as in Example 4, 88 mg (yield: 38%) of the title compound was obtained as a pale yellow amorphous powder from 191 mg (0.73 mmol) of 5-(3,4,5-trimethoxyphenyl)penta-(2E,4E)-dienoic acid and 72 mg (0.33 mmol) of trans-1-benzyl-3,4-bis(aminomethyl)pyrrolidine synthesized by the process described in Referential Example 1.

$^1$H-NMR (DMSO-d$_6$, 120° C.) δ: 1.98–2.13(m,2H), 2.36 (dd,J=9.1,5.4 Hz,2H), 2.71(dd,J=9.1,7.1 Hz,2H), 3.19(ddd, J=13.3,6.1,6.1 Hz,2H), 3.25(ddd,J=13.3,6.1,6.1 Hz,2H), 3.58(s,2H), 3.72(s,6H), 3.80(s,12H), 6.11(d,J=15.1 Hz,2H), 6.77(d,J=15.1 Hz,2H), 6.78(s,4H), 6.86(dd,J=15.1,9.4 Hz,2H), 7.12–7.32(m,5H), 7.15(dd,J=15.1,9.4 Hz,2H), 7.58 (br t,J=6.1 Hz,2H).

Referential Example 2
Preparation of trans-1-methyl-3,4-bis(tert-butoxycarbonylaminomethyl)pyrrolidine:

A solution of 304 mg (1.4 mmol) of trans-1-benzyl-3,4-bis(aminomethyl)-pyrrolidine synthesized by the process described in Referential Example 1 in 1,4-dioxane (5 ml) was cooled in an ice bath. To the solution were added 4.2 ml (4.2 mmol) of a 1N aqueous solution of sodium hydroxide and 917 mg (4.2 mmol) of di-tert-butyl dicarbonate, and the mixture was stirred for 1 hour. The ice bath was removed, and the mixture was stirred for 24 hours at room temperature. The reaction mixture was then extracted with chloroform. An organic layer was dried over anhydrous sodium sulfate and then concentrated under reduced pressure. The resultant crude oil was purified by column chromatography process described above in acetonitrile (1.5 ml) were added 0.20 ml (2.7 mmol) of a 37% aqueous solution of formaldehyde and 46.9 mg (0.75 mmol) of sodium cyanoborohydride. The mixture was stirred for 20 minutes at room temperature. Acetic acid was then added to the resultant solution to adjust its pH to about 5. The solution was stirred for an additional 30 minutes at room temperature. A 1N aqueous solution of sodium hydroxide was added to the reaction mixture to adjust the pH of the reaction mixture to about 10, and extraction was then conducted with chloroform. An organic layer was dried over anhydrous sodium sulfate and then concentrated under reduced pressure. The resultant crude oil was purified by column chromatography on silica gel to obtain 90.1 mg (yield: 60%) of crude crystals of the title compound.

Example 44
Preparation of trans-1-methyl-3,4-bis[5-(3,4,5-trimethoxyphenyl)penta-(2E,4E)-dienoylaminomethyl]pyrrolidine:

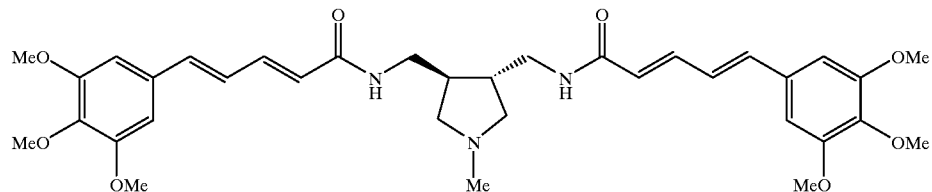

A solution of 81 mg (0.24 mmol) of trans-1-methyl-3,4-bis(tert-butoxycarbonylaminomethyl)pyrrolidine synthesized by the process described in Referential Example 2 in methylene chloride (1 ml) was cooled in an ice bath. To the solution was added trifluoroacetic acid (0.5 ml), and the mixture was stirred for 2 hours. The reaction mixture was concentrated under reduced pressure to obtain an oil containing trans-1-methyl-3,4-bis(aminomethyl)pyrrolidine tritrifluoroacetate. In accordance with the same process as in Example 4, 97 mg (yield: 64%) of crude crystals of the title compound were obtained from this oil and 153 mg (0.58 mmol) of 5-(3,4,5-trimethoxyphenyl)penta-(2E,4E)-dienoic acid. The crude crystals were recrystallized from chloroform-diethyl ether, thereby obtaining a colorless crystalline powder.

Melting point: 197–200° C.

$^1$H-NMR (DMSO-$d_6$, 120° C.) δ: 1.97–2.12(m,2H), 2.25 (s,3H), 2.30(dd,J=9.2,5.0 Hz,2H), 2.64(dd,J=9.2,6.4 Hz,2H), 3.12–3.29(m,4H), 3.72(s,6H), 3.80(s,12H), 6.12(d, J=15.1 Hz,2H), 6.78(d,J=15.6 Hz,2H), 6.79(s,4H), 6.87(dd, J=15.6,9.6 Hz,2H), 7.16(dd,J=15.1,9.6 Hz,2H), 7.59(br t,J= 5.4 Hz,2H).

Referential Example 3

Preparation of trans-3,4-bis(tert-butoxycarbonylamino)-1-methylpyrrolidine:

Added to a solution of 770 mg (2.5 mmol) of trans-3,4-bis(tert-butoxycarbonylamino)pyrrolidine[1] in acetonitrile (11 ml) were 1.1 ml (15 mmol) of a 37% aqueous solution of formaldehyde and 270 mg (4.3 mmol) of sodium cyanoborohydride. The mixture was stirred for 20 minutes at room temperature. Acetic acid was then added to the resultant solution to adjust its pH to about 5. The solution was stirred for an additional 30 minutes at room temperature. A 2.5N aqueous solution of sodium hydroxide was added to the reaction mixture to adjust the pH of the reaction mixture to about 10, and extraction was then conducted with chloroform. An organic layer was dried over anhydrous sodium sulfate and then concentrated under reduced pressure. The resultant crude oil was purified by column chromatography on silica gel to obtain 730 mg (yield: 91%) of the title compound as a colorless oil.

(1) Yoon, S.; Still, W. C., Tetrahedron, 1995, 51, 567–578.

Example 45

Preparation of trans-3,4-bis[5-(3,4,5-trimethoxyphenyl)penta-(2E,4E)-dienoylamino]-1-methylpyrrolidine hydrochloride:

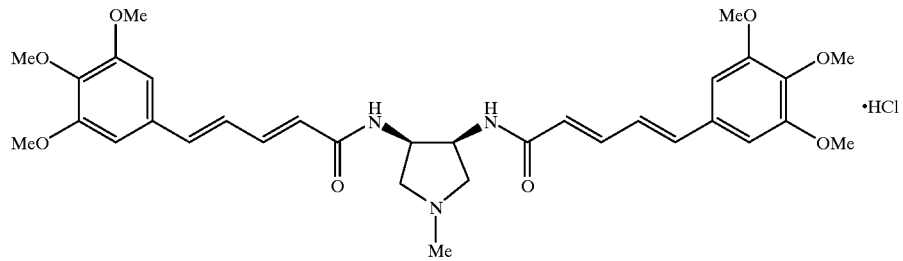

A 4N ethyl acetate solution (2 ml) of hydrogen chloride was added to a solution of 100 mg (0.32 mmol) of trans-3,4-bis(tert-butoxycarbonylamino)-1-methylpyrrolidine synthesized by the process described in Referential Example 3 in tetrahydrofuran (2 ml). The mixture was stirred for 2 hours at room temperature and for additional 30 minutes at 50° C. The reaction mixture was concentrated under reduced pressure, thereby obtaining 80 mg of oil containing trans-3,4-diamino-1-methylpyrrolidine trihydrochloride. In accordance with the same process as in Example 4, 66 mg (yield: 34%) of trans-3,4-bis[5-(3,4,5-trimethoxyphenyl)penta-(2E, 4E)-dienoylamino]-1-methyl-pyrrolidine was obtained as a pale yellow amorphous powder from 80 mg of this oil and 184 mg (0.70 mmol) of 5-(3,4,5-trimethoxyphenyl)penta-(2E,4E)-dienoic acid. To a solution of the thus-obtained amorphous powder in ethanol (1 ml) was added 0.10 ml (0.10 mmol) of 1N hydrochloric acid, and the resultant mixture was concentrated under reduced pressure, thereby obtaining the title compound as a pale yellow amorphous powder.

$^1$H-NMR (data for free base of the title compound) (DMSO-d$_6$, 120° C.) δ: 2.27(s,3H), 2.60–2.70(m,2H), 3.10–3.20(m,2H), 3.72(s,6H), 3.82(s,12H), 4.20–4.30(m,2H), 6.13(d,J=15.9 Hz,2H), 6.81(s,4H), 6.73–6.92(m,4H), 7.16(dd,J=15.0,10.0 Hz,2H), 7.80–7.90(m,2H).

Example 46

Preparation of N,N'-bis[3-(3,4,5-trimethoxyphenyl)-2-propynoyl]-1,3-diaminopropane:

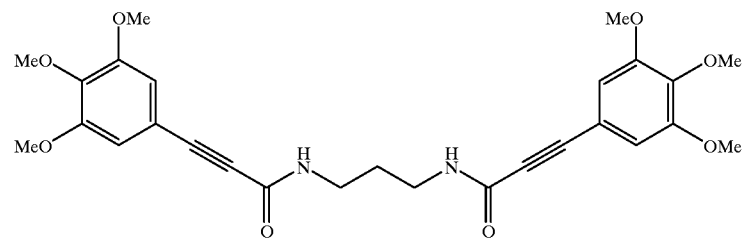

In accordance with the same process as in Example 1, crude crystals were obtained from 260 mg (1.1 mmol) of 3-(3,4,5-trimethoxyphenyl)-2-propynoic acid and 37 mg (0.51 mmol) of 1,3-diaminopropane. The crude crystals were recrystallized from acetone-diethyl ether, thereby obtaining 118 mg (yield: 46%) of the title compound as a colorless crystalline powder.

Melting point: 158–160° C.

$^1$H-NMR (CDCl$_3$) δ: 1.78(br tt,J=6.2,6.2 Hz,2H), 3.46(br dt,J=6.2,6.2 Hz,4H), 3.85(s,12H), 3.88(s,6H), 6.56(br t,J=6.2 Hz,2H), 6.79(s,4H).

Example 47

Preparation of N,N'-bis[5-(3,4,5-trimethoxyphenyl)pent-(2E)-ene-4-ynoyl]-1,2-diaminobenzene:

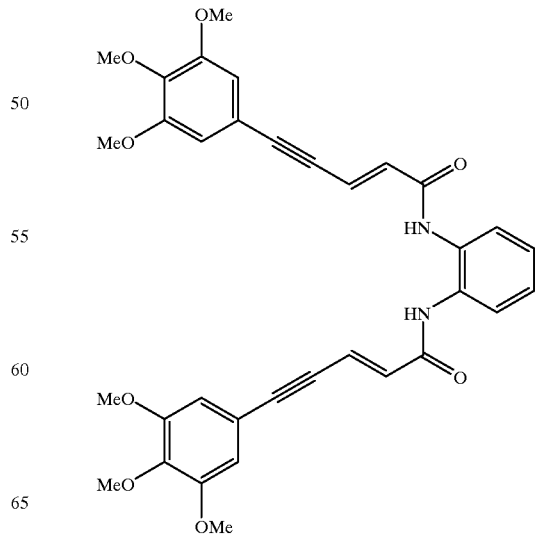

In accordance with the same process as in Example 4, 92 mg (yield: 77%) of crude crystals of the title compound were obtained from 115 mg (0.44 mmol) of 5-(3,4,5-trimethoxyphenyl)pent-(2E)-ene-4-ynoic acid and 22 mg (0.20 mmol) of 1,2-diaminobenzene. The crude crystals were recrystallized from ethyl acetate-hexane, thereby obtaining a pale yellow needles.

Melting point: 232–234° C.

$^1$H-NMR (DMSO-$d_6$, 120° C.) δ: 3.74(s,6H), 3.80(s, 12H), 6.70(d,J=15.6 Hz,2H), 6.87(d,J=15.6 Hz,2H), 7.15–7.21(m,2H), 7.64–7.71(m,2H), 9.33(br s,2H).

Example 48

Preparation of trans-N,N'-bis[3-(3,4-dihydro-6,7,8-trimethoxy-2-naphthyl)prop-(2E)-enoyl]-1,2-diaminocyclohexane:

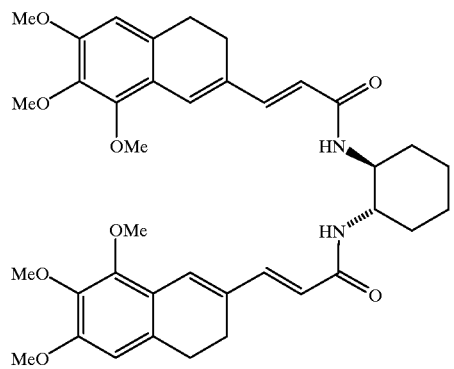

In accordance with the same process as in Example 4, 165 mg (yield: 99%) of crude crystals of the title compound were obtained from 160 mg (0.55 mmol) of 3-(3,4-dihydro-6,7,8-trimethoxy-2-naphthyl)prop-(2E)-enoic acid and 29 mg (0.25 mmol) of trans-1,2-diaminocyclohexane. The crude crystals were recrystallized from chloroform-hexane, thereby obtaining a pale yellow crystalline powder.

Melting point: 189–191° C.

$^1$H-NMR (DMSO-$d_6$, 120° C.) δ: 1.23–1.38(m,4H), 1.60–1.75(m,2H), 1.90–2.00(m,2H), 2.36(dd,J=8.0,8.0 Hz,4H), 2.74(dd,J=8.0,8.0 Hz,4H), 3.40–3.55(m,2H), 3.73 (s,6H), 3.78(s,6H), 3.81(s,6H), 6.04(d,J=15.4 Hz,2H), 6.60 (s,2H), 6.83(s,2H), 7.18(d,J=15.4 Hz,2H), 7.35–7.42(m, 2H).

Example 49

Preparation of 1,4-bis[3-(6,7,8-trimethoxy-2-naphthyl)prop-(2E)-enoylaminomethyl]cyclohexane:

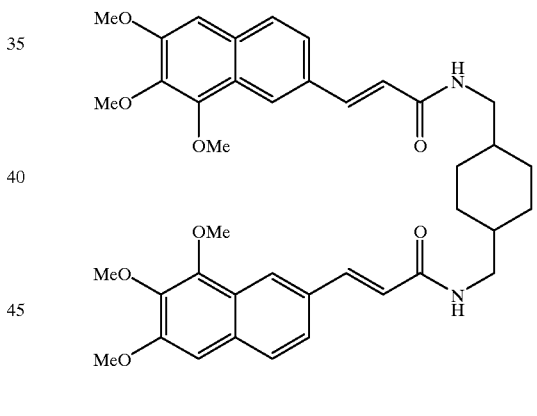

In accordance with the same process as in Example 4, 40 mg (yield: 60%) of the title compound was obtained as a pale yellow amorphous powder from 60 mg (0.21 mmol) of 3-(6,7,8-trimethoxy-2-naphthyl)prop-(2E)-enoic acid and 14 mg (0.10 mmol) of 1,4-bis(aminomethyl)cyclohexane.

$^1$H-NMR (DMSO-$d_6$, 120° C.) (mixture of diastereomers; mixture of amide rotamers; no amide C(O)NH proton was observed) δ: 1.43–1.55(m,8H), 1.75–1.85(m,2H), 3.09(m, 1H), 3.20(m,1H), 3.45–3.53(m,2H), 3.88(s,6H), 3.93(s,6H), 4.00(s,6H), 6.69(d,J=15.6 Hz,2H), 7.50–7.56(m,2H), 7.57–7.65(m,2H), 7.12(s,2H), 7.74(d,J=8.5 Hz,2H), 8.04(s, 2H).

Example 50

Preparation of N,N-bis[N-[3-(5,6-dimethoxy-1,1-dimethyl-2-indenyl)prop-(2E)-enoyl]-3-aminopropyl]methylamine:

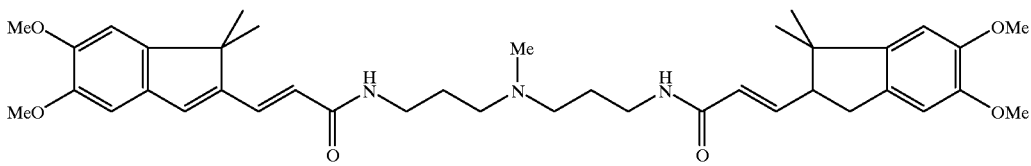

In accordance with the same process as in Example 1, 30 mg (yield: 95%) of the title compound was obtained as a pale yellow amorphous powder from 30 mg (0.11 mmol) of 3-(5,6-dimethoxy-1,1-dimethyl-2-indenyl)prop-(2E)-enoic acid and 7.0 mg (0.048 mmol) of N,N-bis(3-aminopropyl) methylamine.

$^1$H-NMR (DMSO-$d_6$, 120° C.) δ: 1.31(s,12H), 1.50–1.68 (m,4H), 2.19(s,3H), 2.38(t,J=7.0 Hz,4H), 3.15–3.25(m,4H), 3.76(s,6H), 3.81(s,6H), 6.30(d,J=16.1 Hz,2H), 6.89(s,2H), 6.98(s,2H) 7.04(s,2H), 7.25(d,J=16.1 Hz,2H), 7.58–7.67(m, 2H).

Example 51

Preparation of N,N'-bis[4-(3,4,5-trimethoxyphenyl)benzoyl]-3,4-diaminopyridine:

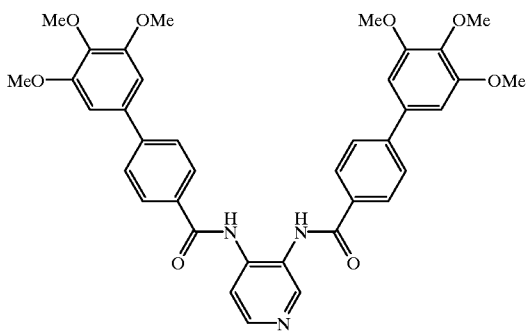

In accordance with the same process as in Example 4, 100 mg (yield: 77%) of crude crystals of the title compound were obtained from 230 mg (0.80 mmol) of 4-(3,4,5-trimethoxyphenyl)benzoic acid and 22 mg (0.20 mmol) of 3,4-diaminopyridine. The crude crystals were recrystallized from ethanol-hexane, thereby obtaining pale yellow needles.

Melting point: 225–226° C.

$^1$H-NMR (mixture of amide rotamers) (DMSO-$d_6$, 120° C.) δ: 3.75(s,3H), 3.76(s,3H), 3.86(s,6H), 3.87(s,6H), 6.96 (s,2H), 6.97(s,2H), 7.74–7.82(m,4H), 7.97(br d,J=5.3 Hz,1H), 7.99(d,J=8.7 Hz,2H), 8.06(d,J=8.7 Hz,2H), 8.41(d, J=5.3 Hz,1H), 8.75(br s,1H), 9.96(br s,2H).

Example 52

Preparation of N,N'-bis[5-nitro-2-(3,4,5-trimethoxyphenyl)benzoyl]ethylenediamine:

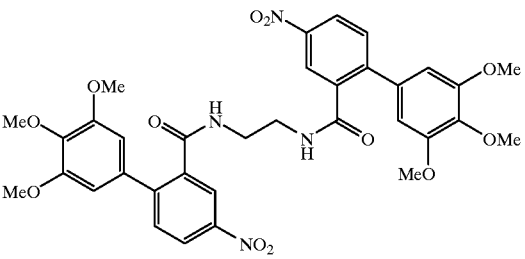

In accordance with the same process as in Example 1, 61 mg (yield: 88%) of crude crystals of the title compound were obtained from 73 mg (0.22 mmol) of 5-nitro-2-(3,4,5-trimethoxyphenyl)benzoic acid and 6.0 mg (0.10 mmol) of ethylenediamine. The crude crystals were recrystallized from methylene chloride-hexane, thereby obtaining a pale yellow crystalline powder.

Melting point: at least 250° C.

$^1$H-NMR (DMSO-$d_6$, 120° C.) δ: 3.13–3.21(m,4H), 3.74 (s,6H), 3.78(s,12H), 6.74(s,4H), 7.68(d,J=8.5 Hz,2H), 7.93–8.01(m,2H), 8.18(d,J=2.4 Hz,2H), 8.23(dd,J=8.5,2.4 Hz,2H).

Example 53

Preparation of N,N'-bis[5-amino-2-(3,4,5-trimethoxyphenyl)benzoyl]ethylenediamine:

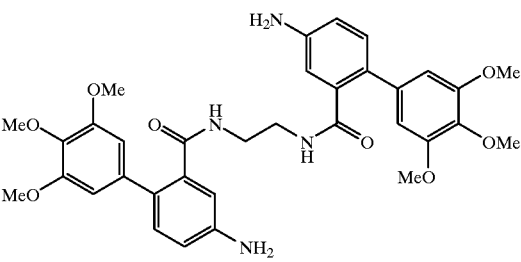

To a solution of 20 mg (0.028 mmol) of N,N'-bis[5-nitro-2-(3,4,5-trimethoxy-phenyl)benzoyl]ethylenediamine synthesized by the process of Example 52 in acetic acid-ethyl acetate (1:3, 2 ml) was added 20 mg of 10% palladium on carbon, and the mixture was stirred for 3 hours at room temperature under hydrogen. The catalyst was removed from the reaction mixture by suction filtration through Celite, and the filtrate was concentrated under reduced pressure. A solution of the resultant residue in chloroform was washed with a saturated solution of a sodium hydrogencarbonate and a saturated saline solution, dried over anhydrous sodium sulfate, and then concentrated under reduced pressure, thereby obtaining 17 mg (quantitative) of crude crystals of the title compound. The crude crystals were recrystallized from methylene chloride-diethyl ether, thereby obtaining a pale yellow crystalline powder.

Melting point: at least 250° C.

$^1$H-NMR (DMSO-$d_6$, 120° C.) δ: 2.98–3.15(m,4H), 3.69 (s,6H), 3.74(s,12H), 4.86(br s,4H), 6.56(s,4H), 6.61(d,J=2.4 Hz,2H), 6.65(dd,J=8.2,2.4 Hz,2H), 7.04(d,J=8.2 Hz,2H), 7.25–7.33(m,2H).

Example 54
Preparation of N,N'-bis[5-(3,4,5-trimethoxyphenyl)-3-pyridinecarbonyl]-N,N'-dimethyl-1,6-diaminohexane:

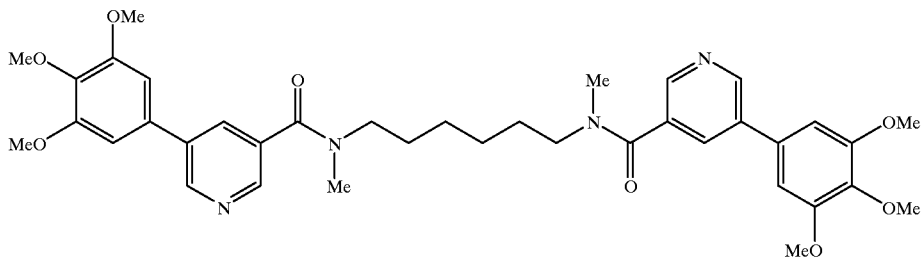

In accordance with the same process as in Example 1, 101 mg (yield: 97%) of the title compound was obtained as a pale yellow amorphous powder from 95 mg (0.33 mmol) of 5-(3,4,5-trimethoxyphenyl)-3-pyridinecarboxylic acid and 22 mg (0.15 mmol) of N,N'-dimethyl-1,6-diaminohexane.

$^1$H-NMR (DMSO-$d_6$, 120° C.) δ: 1.22(t,J=6.8 Hz,4H), 1.49–1.64(m,4H), 2.91(s,6H), 3.23–3.40(m,4H), 3.75(s,6H), 3.83(s,12H), 6.96(s,4H), 7.97(dd,J=2.1,1.9 Hz,2H), 8.48(d,J=1.9 Hz,2H), 8.88(d,J=2.1 Hz,2H).

Example 55
Preparation of 1,4-bis[4-fluoro-3-(3,4,5-trimethoxyphenyl)benzoylaminomethyl]benzene:

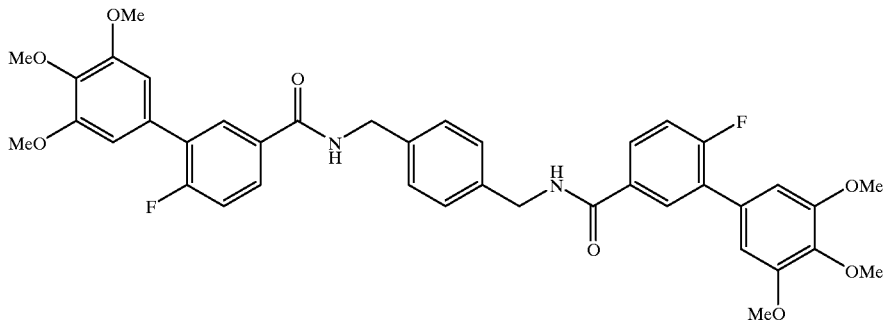

In accordance with the same process as in Example 1, 130 mg (yield: 91%) of the title compound was obtained as a colorless amorphous powder from 135 mg (0.44 mmol) of 4-fluoro-3-(3,4,5-trimethoxyphenyl)benzoic acid and 27 mg (0.20 mmol) of 1,4-bis(aminomethyl)benzene.

$^1$H-NMR (DMSO-$d_6$, 120° C.) δ: 3.76(s,6H), 3.82(s,12H), 4.47(d,J=5.9 Hz,4H), 6.82 (s,2H), 6.83(s,2H), 7.28(dd,J=10.4,8.5 Hz,2H), 7.29(s,4H), 7.87(ddd,J=8.5,4.8,2.4 Hz,2H), 7.98(dd,J=7.5,2.4 Hz,2H), 8.63(br t,J=5.9 Hz,2H).

Example 56
Preparation of N,N'-bis[4-methyl-3-(3,4,5-trimethoxyphenyl)benzoyl]ethylenediamine:

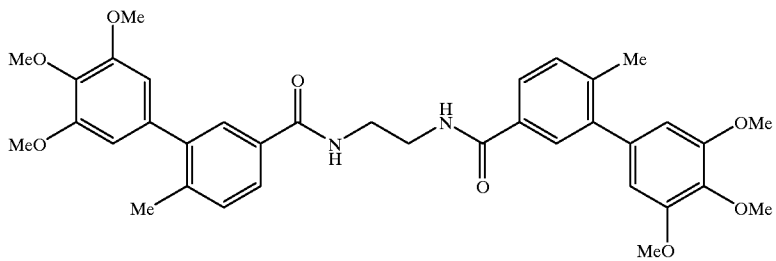

In accordance with the same process as in Example 1, 100 mg (yield: 79%) of crude crystals of the title compound were obtained from 133 mg (0.44 mmol) of 4-methyl-3-(3,4,5-trimethoxyphenyl)benzoic acid and 12 mg (0.20 mmol) of ethylenediamine. The crude crystals were recrystallized from ethanol-hexane, thereby obtaining a colorless crystalline powder.

Melting point: 204–206° C.

$^1$H-NMR (mixture of amide rotamers) (DMSO-$d_6$, 120° C.) δ: 2.27(s,6H), 3.47–3.49(m,4H), 3.75(s,6H), 3.79(s, 12H), 6.57(s,4H), 7.30(d,J=7.8 Hz,2H), 7.68(br d,J=1.9 Hz,2H), 7.69(br dd,J=7.8,1.9 Hz,2H), 8.07–8.17(m,2H).

Example 57
Preparation of N,N'-bis[4-methoxy-3-(3,4,5-trimethoxyphenyl)benzoyl]-1,4-diaminobenzene:

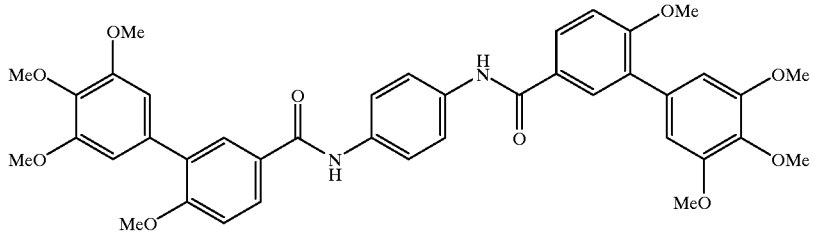

In accordance with the same process as in Example 4, crude crystals were obtained from 98 mg (0.31 mmol) of 4-methoxy-3-(3,4,5-trimethoxyphenyl)benzoic acid and 25 mg (0.14 mmol) of 1,4-diaminobenzene dihydrochloride. The crude crystals were recrystallized from methanol-chloroform-diethyl ether, thereby obtaining 52 mg (yield: 53%) of the title compound as a pale yellow crystalline powder.

Melting point: at least 250° C.

$^1$H-NMR (DMSO-$d_6$, 120° C.) δ: 3.77(s,6H), 3.83(s, 12H), 3.86(s,6H), 6.83(s,4H), 7.19(d,J=8.5 Hz,2H), 7.69(s, 4H), 7.94(d,J=2.0 Hz,2H), 7.96(dd,J=8.5,2.0 Hz,2H), 9.73 (s,2H).

Test Example 1
Evaluation of Inhibitory Effect on Production of IgE Antibody:

A spleen was enucleated from a mouse (Balb/C, male, aged 8 weeks) and shredded in 0.3% BSA/HBSS to prepare single cells by means of a 200-mesh screen. Further, the single cells were hemolyzed by 0.75% ammonium chloride-17 mM Tris solution to prepare a splenocyte suspension ($1 \times 10^7$/ml) using RPMI 1640 medium/25 mM HEPES/0.3% BSA. After the suspension was reacted with a mouse anti-mouse Thy-1.2 monoclonal antibody (product of Cedarlane Co.) at 4° C. for 1 hour, the reaction mixture was centrifuged, and the sediment cells were suspended again ($1 \times 10^7$/ml, RPMI/HEPES/BSA). After the suspension was then reacted with a low-cytotoxic rabbit complement (product of Cedarlane Co.) at 37° C. for 1 hour, killed cells were removed by specific gravity centrifugation using lympholyte M (product of Cedarlane Co.) to obtain a B cell fraction as viable cells.

After B cells ($10^5$/0.2 ml/well) were cultured for a day together with LPS (E. coli 026:B6, product of DIFCO Co.) using a 96-well plate, mouse IL-4 (product of Genzyme Co.) was added to conduct culture further for 7 days.

Each test agent was added on the first day of the culture, and the amount of IgE in a culture supernatant was measured by ELISA after the culture, thereby calculating out the inhibitory effect of the agent on the production of an IgE antibody. The inhibitory activities of the test agents at a concentration of $10^{-5}$ M are shown in Table 1.

TABLE 1

| Test compound (Example No.) | Inhibitory effect on production of IgE (%) |
| --- | --- |
| 5 | 90 |
| 15 | 100 |
| 22 | 90 |
| 26 | 85 |
| 38 | 80 |

The diamide compounds (1) according to the present inventions have an inhibitory effect on the production of an IgE antibody and are hence useful as agents for preventing snf treating various allergic immunological diseases in which IgE participates, such as asthma.

What is claimed is:

1. A compound having the formula (1):

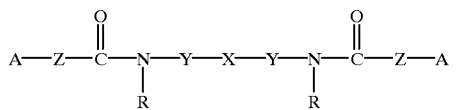

wherein A is phenyl, naphthyl, dihydronaphthyl, indenyl, pyridyl, indolyl, isoindolyl, quinolyl or isoquinolyl, which are each optionally substituted with the group selected from the group consisting of halogen, lower alkoxy, lower alkylthio, amino which is optionally substituted with 1 or 2 lower alkyl, alkyl which is optionally substituted by 1 to 3 halogen; and lower alkythio;

X is lower alkylene which is optionally substituted or lower alkylimino;

Y is a single bond or lower alkylene;

Z is an unsubstituted aliphatic group or a divalent residue of benzene or pyridine which are each optionally substituted by halogen, lower alkyl, lower alkoxy, amino or nitro; and R is hydrogen, lower alkyl of at least two carbon atoms, cycloalkyl, aryl or aralkyl, with the proviso that A is not phenyl, a 4-chlorophenyl or a 4-methoxyphenyl when X is ethylene, Y is a single bond, Z is —C≡C—, and R is hydrogen; A is not 3,4-dichlorophenyl when X is trimethylene, Y is a single bond, Z is —(CH=CH)$_2$—, and R is hydrogen; and A is not 3,4-dihydroxyphenyl, 3-hydroxy-4-methoxyphenyl, 3-methoxy-4-hydroxyphenyl, or 3,4-dimethoxyphenyl when X is tetramethylene, Y is a single bond, Z is —CH=CH— or —(CH=CH)$_2$—, and R is hydrogen; or a salt or solvate thereof.

2. The compound of claim 1, wherein X is a lower alkylene group which is optionally substituted by carboxyl or lower alkoxy carbonyl.

3. The compound of claim 1, wherein X is a divalent residue of a cycloalkane having 5 to 8 carbon atoms which is optionally substituted by halogen, hydroxyl, lower alkyl which is optionally substituted by a primary, secondary or tertiary amino group, lower alkoxy, carboxyl, lower alkoxy carbonyl, amino, alkylamino, dialkylamino, nitro, cyano or aralkyl.

4. The compound of claim 1, wherein said lower alkyl of A, Z and R is C$_1$–C$_6$ alkyl.

5. The compound of claim 1, wherein said lower alkoxy of A and Z is C$_1$–C$_6$ alkoxy.

6. The compound of claim 1, wherein said lower alkylene of X and Y is C$_1$–C$_8$ linear or branched alkylene.

7. The compound of claim 1, wherein said cycloalkyl of R is C$_3$–C$_8$ cycloalkyl.

8. The compound of claim 1, wherein said aryl of R has 6 to 14 carbon atoms.

9. The compound claim 8, wherein said aryl is phenyl or naphthyl.

10. The compound of claim 9, wherein said aralkyl is C$_6$–C$_{14}$ aryl-C$_1$–C$_8$ alkyl.

11. The compoundof claim 1, wherein A is phenyl substituted by 1 to 3 substituents selected from the group consisting of lower alkyl and lower alkoxy.

12. The compound of claim 6, wherein said lower alkylene is C$_2$ or C$_5$–C$_8$ alkylene, which is optionally substituted.

13. The compound of claim 12, wherein said lower alkylene is substituted by carboxyl or lower alkoxycarbonyl.

14. The compound of claim 1, which is selected from the group consisting of N,N'-bis[5-(3,4,5-trimethoxyphenyl)-penta-(2E,4E)-dienoyl]-N,N'-dibenzylethylenediamine, N,N'-bis[5-(3,4,5-trimethoxyphenyl)-penta-(2E,4E)-dienoyl]-N,N'-dimethyl-1,6-diaminohexane, N,N'-bis[5-(3,4,5-trimethoxyphenyl)-penta-(2E,4E)-dienoyl]-1,4-diaminocyclohexane, trans-N,N'-bis[5-(3,4,5-trimethoxyphenyl)penta-(2E,4E)-dienoyl]-1,2-diaminocyclohexane, N,N'-bis[5-(3,4,5-trimethoxyphenyl)-penta-(2E,4E)-dienoyl]-1,4-bis(aminomethyl)benzene, N,N'-bis[5-(3,4,5-trimethoxybpenyl)-penta-(2E,4E)-dienoyl]-1,2-diaminobenzene, N,N'-bis[5-(3,4,5-trimethoxyphenyl)-penta-(2E,4E)-dienoyl]-2,3-diaminophenol, trans-N,N'bis[3-(3,4-dihydro-6,7,8-trimethoxy-2-naphthyl)prop-2(2E)-enoyl]-1,2-diaminocyclohexane, 1,4-bis[3-(6,7,8-trimethoxy-2-naphthyl)prop-(2E)-enoylaminomethyl]cyclohexane, N,N'-bis[4-(3,4,5-trimethoxyphenyl)-benzoyl]-3,4-diaminopyridine, 1,4-bis[4-fluoro-3-(3,4-diaminopyridine, 1,4-bis[4-fluoro-3-(3,4,5-trimethoxyphenyl) benzoylaminomethyl]benzene, and N,N'-bis[4-methoxy-3-) 3,4,5-trimethoxyphenyl)benzoyl]-1,4-diaminobenzene.

15. The compound of claim 1, wherein said solvate is a hydrate.

16. A pharmaceutical composition, comprising the compound of claim 1, and a pharmaceutically-acceptable carrier.

17. A method of treating an allergic immunological disease, which comprises administering an effective amount of one or more compounds of claim 1, to a mammal in need thereof.

18. The method of claim 17, wherein said mammal is a human.

* * * * *

UNITED STATES PATENT AND TRADEMARK OFFICE
CERTIFICATE OF CORRECTION

PATENT NO.   : 6,297,283 B1
DATED        : October 2, 2001
INVENTOR(S)  : Ishiwata et al.

It is certified that error appears in the above-identified patent and that said Letters Patent is hereby corrected as shown below:

Column 53,
Line 12, delete "are each optionally substituted with the group selected from" and replace with -- is optionally substituted with a group selected from --;
Line 16, delete "and lower alkythio;";
Line 24, delete "R is hydrogen, lower alkyl of at least two carbon atoms" and replace with -- R is hydrogen, lower alkyl --.

Column 54,
Line 9, delete "compoundof" and replace with -- compound of --;
Lines 26-39, after "diaminocyclohexane", delete in its entirety and replace with -- trans-N,N'bis (3-3,4-dihydro-6,7,8-trimethoxy-2-naphthyl) prop-2(2E)-enoyl)-1,2-diaminocyclohexane, and 1,4-bis (3-(6,7,8-trimethoxy-2-naphthyl) prop-(2E)-enoylaminomethyl) cyclohexane. --

Signed and Sealed this

First Day of October, 2002

Attest:

JAMES E. ROGAN
Attesting Officer
Director of the United States Patent and Trademark Office